US012458797B2

(12) United States Patent
Bauer et al.

(10) Patent No.: US 12,458,797 B2
(45) Date of Patent: Nov. 4, 2025

(54) CATHETER AND LEADS FOR CARDIAC CONDUCTION SYSTEM

(71) Applicant: Singular Medical (USA) Inc., Irvine, CA (US)

(72) Inventors: Ryan Bauer, Irvine, CA (US); Scott Hayden, Irvine, CA (US); Yongxing Zhang, Irvine, CA (US); Martin Tze, Irvine, CA (US); Entao Liu, Irvine, CA (US); Lichuan Ping, Irvine, CA (US)

(73) Assignee: SINGULAR MEDICAL (USA) INC., Irvine, CA (US)

( * ) Notice: Subject to any disclaimer, the term of this patent is extended or adjusted under 35 U.S.C. 154(b) by 396 days.

(21) Appl. No.: 17/804,705

(22) Filed: May 31, 2022

(65) Prior Publication Data

US 2023/0381502 A1 Nov. 30, 2023

(51) Int. Cl.
*A61N 1/05* (2006.01)

(52) U.S. Cl.
CPC .................................. *A61N 1/0575* (2013.01)

(58) Field of Classification Search
CPC ............................ A61N 1/0575; A61N 1/0573
See application file for complete search history.

(56) References Cited

U.S. PATENT DOCUMENTS

| | | | | |
|---|---|---|---|---|
| 5,425,755 A | | 6/1995 | Doan | |
| 5,545,201 A | | 8/1996 | Helland et al. | |
| 10,881,352 B2 | | 1/2021 | Hara | |
| 11,446,486 B1 | * | 9/2022 | Dandamudi | A61N 1/0573 |
| 2002/0151934 A1 | | 10/2002 | Levine | |
| 2010/0114280 A1 | * | 5/2010 | Hill | A61N 1/0573 607/116 |
| 2017/0072191 A1 | * | 3/2017 | Ma | A61N 1/3756 |

FOREIGN PATENT DOCUMENTS

| | | | |
|---|---|---|---|
| CN | 111714774 | A | 9/2020 |
| CN | 113289244 | A | 8/2021 |
| CN | 217430666 | U | 9/2022 |
| JP | 60-249237 | A | 12/1985 |
| JP | 2012-204035 | A | 10/2012 |
| JP | 2017-139187 | A | 8/2017 |
| RU | 2147246 | C1 | 4/2000 |

OTHER PUBLICATIONS

International Search Report and Written Opinion, International Patent Application No. PCT/US23/67698, Jan. 31, 2024 (10 pages).

* cited by examiner

*Primary Examiner* — Joseph M Dietrich
(74) *Attorney, Agent, or Firm* — HSML P.C.

(57) ABSTRACT

A lead for cardiac conduction system includes a proximal end, a lead body extending from the proximal end, and a distal end extending from the lead body. The lead body includes a non-conductive spacer. The distal end includes a helix electrode distal to the spacer. The lead further includes a ring electrode proximal to the spacer and surrounding a portion of the lead body. The helix electrode includes a core disposed within a helical space of the helix electrode. Another lead for cardiac conduction system includes a proximal end, a lead body extending from the proximal end, and a distal end extending from the lead body. The distal end includes a first helix electrode extending from the lead body and a second helix electrode extending from the lead body. A tip of the first helix electrode is distal to a tip of the second helix electrode.

7 Claims, 14 Drawing Sheets

CATHETER AND LEADS FOR CARDIAC CONDUCTION SYSTEM

FIELD

This disclosure relates generally to systems, methods, and designs of catheter and lead(s) for the cardiac conduction system. More specifically, the disclosure relates to systems and designs of catheter and lead(s) for the cardiac conduction system, and relates to methods of implanting lead(s) for the cardiac conduction system using a catheter system including the catheter.

BACKGROUND

An implantable pulse generator (e.g., an implantable pacemaker, an implantable cardioverter-defibrillator, etc.) is a medical device powered by a battery, contains electronic circuitry having a controller, and delivers and regulates electrical impulses to an organ or a system such as the heart, the nervous system, or the like. A lead is a thin, flexible, electrical wire connecting a device such as the implantable pulse generator to a target such as the organ or system, transmits electrical impulses (e.g., a burst of energy) from the device to the target, and/or senses or measures the potential or the voltage from the target. A catheter is a tubular medical device for insertion into canals, vessels, passageways, or body cavities usually to keep a passage open to facilitate the delivery of e.g., a lead or leads during a surgical procedure. The process of inserting a catheter is “catheterization”. The conduction system of the heart consists of cardiac muscle cells and conducting fibers that are specialized for initiating impulses and conducting the impulses through the heart. The cardiac conduction system initiates the normal cardiac cycle, coordinates the contractions of cardiac chambers, and provides the heart its automatic rhythmic beat. Conduction system pacing (CSP) is a technique of pacing that involves implantation of pacing leads along different sites or pathways of the cardiac conduction system and includes His-bundle pacing, left bundle branch pacing, right bundle branch pacing, and/or bilateral pacing (pacing both the left bundle branch and the right bundle branch).

SUMMARY

This disclosure relates generally to systems, methods, and designs of catheter and lead(s) for the cardiac conduction system. More specifically, the disclosure relates to systems and designs of catheter and lead(s) for the cardiac conduction system, and relates to methods of implanting lead(s) for the cardiac conduction system using a catheter system including the catheter.

In an embodiment, a catheter system for implanting a lead for cardiac conduction system is disclosed. The catheter system includes a catheter having an orifice extending from a distal end of the catheter to a proximal end of the catheter for implanting the lead, and a probe extending through the catheter. The probe includes a conductive wire (made of metal or any other suitable materials) covered with an insulation layer. A distal end of the wire is exposed from the insulation layer. The distal end of the wire includes an electrode configured to conduct pacing prior to implanting the lead.

In an embodiment, a method of implanting a lead for cardiac conduction system using a catheter system is disclosed. The method includes inserting a catheter to reach septum. The method also includes placing a probe inside the catheter lumen or independent of the catheter to reach and electrically map the cardiac conduction system. The probe includes a conductive wire covered with an insulation layer. A distal end of the wire is exposed from the insulation layer. The distal end of the wire includes an electrode. The method further includes dispositioning the probe into the septum, conducting pacing through the probe to the septum, conducting sensing to obtain electrocardiogram during or after the pacing, adjusting a location of the probe based on the obtained electrocardiogram, inserting the lead through an orifice of the catheter extending from a distal end of the catheter to a proximal end of the catheter, and placing a distal end of the lead to the adjusted location.

In an embodiment, a lead for cardiac conduction system is disclosed. The lead includes a lead body having a first diameter, a distal end including a helix electrode having a second diameter, and a proximal end. The second diameter is equal to, smaller than, or greater than the first diameter.

In an embodiment, a lead for cardiac conduction system. The lead includes a lead body, a distal end including a linear electrode having a tapered tip and a rod integral to the tapered tip, and a proximal end. A helix wire is wrapped around the rod of the linear electrode.

In an embodiment, a lead for cardiac conduction system is disclosed. The lead includes a lead body, a distal end including and a first helix electrode and a second helix electrode, and a proximal end. The first helix electrode and the second helix electrode are fixed to the lead body. A coil of the first helix electrode and a coil of the second helix electrode extend distally from the lead body and wind alongside with each other. The coil of the first helix electrode extends further distally than the coil of the second helix electrode.

In an embodiment, a lead for cardiac conduction system is disclosed. The lead includes a lead body. The lead also includes a distal end including a linear electrode having a tapered tip and a rod integral to the tapered tip, a spacer connected to the linear electrode, and a helix electrode fixed to the lead body. The lead further includes a proximal end. The spacer is adjustable to distally extend or proximally retract the linear electrode.

In an embodiment, a method of implanting a lead for cardiac conduction system using a catheter system is disclosed. The method includes inserting a catheter to reach septum, positioning the catheter against the septum, inserting the lead through an orifice of the catheter extending from a distal end of the catheter to a proximal end of the catheter, rotating a lead body of the lead to engage a helix electrode of the lead to the septum, and removing the catheter.

In an embodiment, a lead for cardiac conduction system is disclosed. The lead includes a lead body. The lead also includes a distal end including a linear electrode having a tapered tip and a rod integral to the tapered tip, a helix electrode fixed to the lead body, and a spacer disposed between the linear electrode and the helix electrode. The lead further includes a proximal end. A length of the spacer is predetermined.

In an embodiment, a lead assembly for cardiac conduction system is disclosed. The lead assembly includes a lead having a lead body, a distal end, and a proximal end. The lead assembly also includes a connector separate from the lead. An outer diameter of the lead body is equal to or greater than an outer diameter of the proximal end. The outer diameter of the lead body is equal to or greater than an outer diameter of the distal end. The proximal end is configured to connect to a first end of the connector. A second end of the connector is configured to connect to a header of an implantable pulse generator.

In an embodiment, a catheter system for implanting a lead for cardiac conduction system is disclosed. The catheter system includes a catheter having an orifice extending from a distal end of the catheter to a proximal end of the catheter for implanting the lead, and a wire extending through the catheter. The wire includes a tapered distal tip configured to penetrate septum.

In an embodiment, a method of implanting a lead for cardiac conduction system using a catheter system is disclosed. The method incudes inserting a catheter to reach ventricular septum, positioning the catheter against the ventricular septum, inserting the lead through an orifice of the catheter extending from a distal end of the catheter to a proximal end of the catheter, engaging an electrode of the lead to the ventricular septum, and removing the catheter.

Embodiments disclosed herein can provide a catheter and lead(s) that can be "deep" seated into the ventricular septum (e.g., inserted inside the ventricular septum in an adequate distance, e.g., the lead body being partially inside the tissue of ventricular septum) of the cardiac conduction system (e.g., to reach the pathway such as the LBB from the cavity of the right ventricle). Embodiments disclosed herein can also provide a catheter and lead(s) that can be more atraumatic and easier to be delivered to a desired location. Embodiments disclosed herein can further provide a catheter and lead(s) that can minimize the trauma to the heart tissue and have stable electrical performance.

Other features and aspects will become apparent by consideration of the following detailed description and accompanying drawings.

BRIEF DESCRIPTION OF THE DRAWINGS

References are made to the accompanying drawings that form a part of this disclosure and which illustrate the embodiments in which systems and methods described in this specification can be practiced.

Figure 1:
FIG. 1 is a side view of a probe for a catheter, according to an embodiment.

Particular embodiments of the present disclosure are described herein with reference to the accompanying drawings; however, it is to be understood that the disclosed embodiments are merely examples of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. In this description, as well as in the drawings, like-referenced numbers represent like elements that may perform the same, similar, or equivalent functions.

DETAILED DESCRIPTION

This disclosure relates generally to systems, methods, and designs of catheter and lead(s) for the cardiac conduction system. More specifically, the disclosure relates to systems and designs of catheter and lead(s) for the cardiac conduction system, and relates to methods of implanting lead(s) for the cardiac conduction system using a catheter system including the catheter.

As defined herein, the phrase "distal" may refer to being situated away from a point of attachment (e.g., to a device such as the implantable pulse generator) or from an operator (e.g., a physician, a user, etc.). A distal end of a lead or a catheter may refer to an end of the lead or the catheter that is away from the operator or from a point of attachment to the implantable pulse generator.

As defined herein, the phrase "proximal" may refer to being situated nearer to a point of attachment (e.g., to a device such as the implantable pulse generator) or to an operator (e.g., a physician, a user, etc.). A proximal end of a lead or a catheter may refer to an end of the lead or the catheter that is close to the operator or to a point of attachment to the implantable pulse generator.

As defined herein, the phrase "French" may refer to a unit to measure the size (e.g., diameter or the like) of device such as a catheter, a lead, etc. For example, a round catheter or lead of one (1) French has an external diameter of ⅓ millimeters. For example, if the French size is 9, the diameter is 9/3=3.0 millimeters.

As defined herein, the phrase "helix" may refer to (e.g., an object) having a three-dimensional shape like that of a wire wound (e.g., in a single layer) around a cylinder or cone, as in a corkscrew or spiral staircase. The phrase "linear" may refer to being arranged in or extending straightly or nearly straightly.

As defined herein, the phrase "conductive" may refer to electrically conductive.

As defined herein, the phrase "septum" may refer to a partition separating two chambers, such as that between the chambers of the heart. Septum can be atrial septum and/or ventricular septum. The phrase "ventricular septum" or "inter-ventricular septum" may refer to a partition separating two ventricular chambers. The phrase "right ventricular septum" may refer to the ventricular septum where the RBB is located, while "left ventricular septum" may refer to the ventricular septum where the LBB is located.

As defined herein, the phrase "pacing" may refer to depolarization of the atria or ventricles, resulting from an impulse delivered (e.g., at desired voltage(s) for a desired duration, or the like) from a device (such as a pulse generator) down a lead to the heart via myocardium or directly via the cardiac conduction system. The phrase "sensing" may refer to detection by the device of intrinsic atrial or ventricular or conduction system electrical signals that are conducted up a lead. It will be appreciated that each of the electrode described herein can be configured as a pacing electrode and/or a sensing electrode. It will also be appreciated that each of the electrode described herein can be configured as anode and/or cathode.

As defined herein, the phrase "conduction system pacing" or "CSP" may refer to a therapy that involves the placement of permanent pacing leads along different sites or pathways of the cardiac conduction system with the intent of overcoming sites of atrioventricular conduction disease and delay, thereby providing a pacing solution that results in more synchronized biventricular activation. Lead placement for CSP can be targeted at the bundle of His, known as His-bundle pacing (HBP), at the region of the left bundle branch (LBB), known as LBB pacing (LBBP), or at the region of the right bundle branch (RBB), known as RBB pacing (RBBP) or both at the regions of RBB and LBB for Bi-lateral Bundle Branch Pacing (BBBP). Compared with conventional right ventricular (RV) pacing or biventricular (RV and left ventricular (LV)) pacing, where RV apical pacing lead and/or LV epicardial lead are implanted, the lead for CSP is placed through the septum e.g., closer to the His-bundle, the LBB, and/or the RBB. As such, the design, function, and purpose of the lead(s) for cardiac conduction system are different from those of the lead(s) for RV and/or LV pacing. It will be appreciated that ventricular pacing (e.g., RV pacing or the like) may be un-physiological and may result in adverse outcomes of mitral and/or tricuspid regurgitations, atrial fibrillation, heart failure, and/or pacing induced cardiomyopathy. CSP can be physiological pacing that can results in electrical-mechanical synchronization to mitigate chronic clinical detrimental consequence including e.g., pacing induced cardiomyopathy. It will also be appreciated that CSP indications may include e.g., a high burden of ventricular pacing being necessary (e.g., permanent atrial fibrillation with atrioventricular block, slowly conducted atrial fibrillation, pacing induced cardiomyopathy, atrioventricular node ablation, etc.); sick sinus syndrome, when atrioventricular node conduction diseases exist; and/or an alternative to biventricular pacing in heart failure patients with bundle branch block, narrow QRS and PR prolongation, biventricular pacing no-responders or patients need biventricular pacing cardiac resynchronization therapy upgrade, or the like.

Some embodiments of the present application are described in detail with reference to the accompanying drawings so that the advantages and features of the present application can be more readily understood by those skilled in the art. The terms "near", "far", "top", "bottom", "left", "right", and the like described in the present application are defined according to the typical observation angle of a person skilled in the art and for the convenience of the description. These terms are not limited to specific directions.

Processes described herein may include one or more operations, actions, or functions depicted by one or more blocks. It will also be appreciated that although illustrated as discrete blocks, the operations, actions, or functions described as being in various blocks may be divided into additional blocks, combined into fewer blocks, or eliminated, depending on the desired implementation. Any features described in one embodiment may be combined with or incorporated/used into the other embodiment, and vice versa. The scope of the disclosure should be determined by the appended claims and their legal equivalents, rather than by the examples given herein. For example, the steps recited in any method claims may be executed in any order and are not limited to the order presented in the claims. Moreover, no element is essential to the practice of the disclosure unless specifically described herein as "critical" or "essential."

Figure 2:
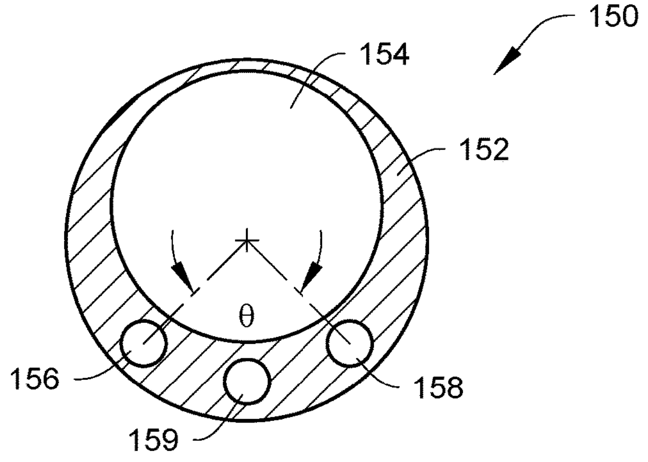
FIG. 2 is a cross-sectional view of a catheter for probe, according to an embodiment.
Figure 3:
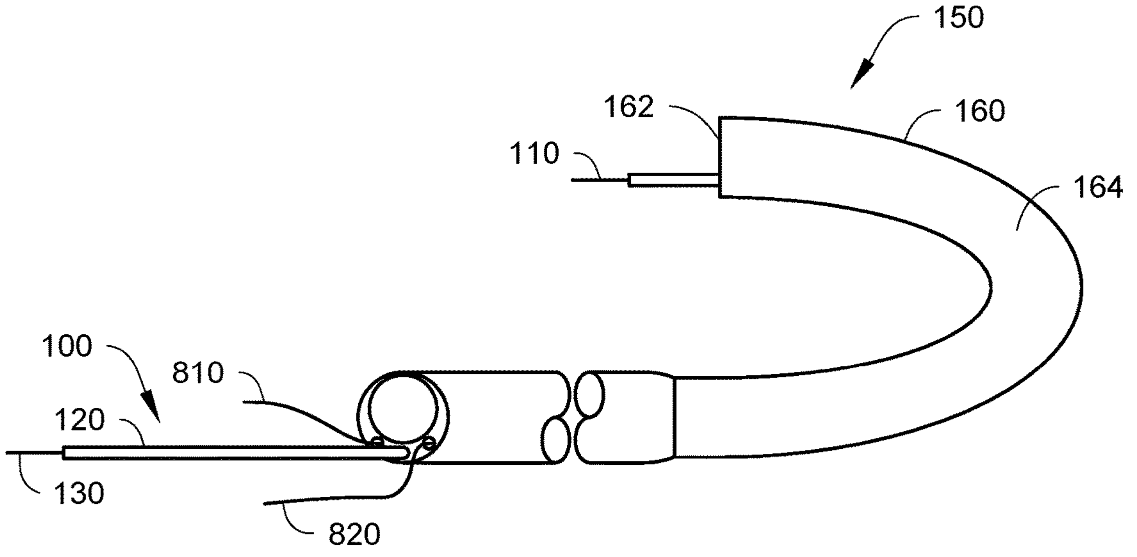
FIG. 3 is a perspective view of a probe for a catheter, according to an embodiment.

FIG. 1 is a side view of a probe 100 for a catheter 150, according to an embodiment. FIG. 2 is a cross-sectional view of the catheter 150, according to an embodiment. FIG. 3 is a perspective view of the catheter 150, according to an embodiment.

As shown in FIG. 1, the probe 100 includes a wire having a distal end 110 and a proximal end 130. In an embodiment, the wire has a diameter ranging from at or about 100 micron to at or about 150 micron. The wire can be made of conductive metal and can be radiopaque to facilitate implanting and/or locating the wire. The probe 100 also includes a non-conductive insulation layer 120 covering the wire. The distal end 110 of the wire can be exposed from the insulation layer 120. The proximal end 130 of the wire can be exposed from the insulation layer 120. The proximal end 130 can be integrated into a connector (not shown) configured to connect to e.g., a signal processing device (having a controller) for mapping the conduction system.

In an embodiment, the distal end 110 of the wire has a length of at or about one millimeter to at or about three millimeters. The insulation layer can have a diameter/thickness of at or about 25 micron. The insulation layer can be made of polytetrafluoroethylene, polyimide, or any other suitable material.

As shown in FIGS. 2 and 3, in a cross-sectional view (e.g., cut by a plane perpendicular to a length of the catheter 150 from its distal end 160 to its proximal end 170), the catheter 150 includes a body (tube) 152 and an orifice (hole, cavity, opening, etc.) 154 extending from a distal end 160 of the catheter 150 to a proximal end 170 of the catheter 150 for implanting a lead. In an embodiment, a diameter of the orifice 154 ranges from at or about five French to at or about six French or more. In an embodiment, the catheter 150 can be made of red rubber, latex, silicone, plastic and/or polyvinyl chloride, or the like.

In an embodiment, the catheter 150 can include an opening (hole, cavity, orifice, etc.) 159 separated from the orifice 154. The opening 159 extends from the distal end 160 of the catheter 150 to the proximal end 170 of the catheter 150 for inserting the probe 100. In another embodiment, the catheter 150 does not have the opening 159, and the probe 100 is mounted to (e.g., integral to, fixed to, etc.) catheter 150.

In an embodiment, the catheter 150 can include an opening (hole, cavity, orifice, etc.) 156 and an opening 158. The opening 156 is configured to accommodate a first deflection wire 810, the opening 158 is configured to accommodate a second deflection wire 820. The first deflection wire 810 and the second deflection wire 820 are configured to be pulled (e.g., by a user such as a physician) to deflect the distal end of the catheter. In another embodiment, the catheter 150 does not have the opening 156 and the opening 158, and the catheter 150 has a fixed curve at its distal end 160.

In an embodiment, one or more tip electrode(s) can be provided on the distal end 162 of the catheter 150 for endocardial electrical mapping.

In an embodiment, the catheter 150 can be of bi-directional deflection on the same plane or on different planes. For example, the first deflection wire 810 is configured to be pulled to deflect the distal end 160 of the catheter 150 in a first plane (e.g., X-Y plane). The second deflection wire 820 is configured to be pulled to deflect the distal end 160 of the catheter 150 in the same X-Y plane, or in a second plane (e.g., Z-Y plane or Z-X plane) perpendicular to the first plane. The first deflection wire 810 and the second deflection wire 820 are spaced apart at a central angle (θ) from a center of the catheter in a cross-sectional view (see FIG. 2). In an embodiment, the angle θ can be at or about 90 degrees to achieve the desired deflection.

In an embodiment, the first deflection wire 810 is configured to be pulled to deflect a tip 162 of the distal end 160 of the catheter 150. The second deflection wire 820 is configured to be pulled to deflect a location 164 of the distal end 160 of the catheter 150. The location 164 is separate from and proximal to the tip 162 of the distal end 160 of the catheter 150. It will be appreciated that the first deflection wire 810 and the second deflection wire 820 connect to the respective location of the catheter 150 so that the respective location of the catheter 150 can be deflected when the corresponding deflection wire is pulled. It will be appreciated that the deflection/bending locations can be at the distal tip 162 and at or about 5 cm to at or about 10 cm proximal to the distal tip (i.e., the location 164).

In an embodiment, the distal end 110 of the wire can include electrode(s) such as pacing electrode(s) and/or sensing electrode(s). The electrode(s) can be of the forms of flexible or printed electrodes (e.g., printed circuits, surface mounted printed circuits, or the like) or any suitable forms. In an embodiment, the distal end 110 of the wire may not include electrode, and the wire itself can be configured for pacing and/or sensing.

In operation, the distal end 110 of the wire can be configured to identify and/or locate a target or desired location (e.g., His bundle, RBB, LBB, etc.) of the cardiac conduction system prior to implanting the lead. Identifying the target location (e.g., His bundle, RBB, LBB, etc.) of the cardiac conduction system can be referred to as "mapping" or "electrically mapping" of the cardiac conduction system. The proximal end 130 of the wire can be configured to connect to a device (implantable or external, not shown) that can be used to control the probe 100.

In operation, before implanting a lead through the orifice 154 of the catheter 150, electrical impulses (e.g., a burst of energy) can be delivered from the device to the target (e.g., the septum) to stimulate the myocardium and/or the cardiac conduction system. During implantation procedure, the catheter 150 can be inserted to reach septum. The probe 110 can be inserted/placed to reach the septum (e.g., via the opening 159 if the probe 100 is not fixed to the catheter 150).

The distal end 110 of the probe 110 can be positioned onto or into the septum (e.g., by placing against the septum or by poking into the septum by a sharp tip of the probe 110). The device can deliver electrical impulses (e.g., a burst of energy) through the probe 100 (from the proximal end 130 to the distal end 110) to the septum (e.g., at or around pathway(s) of the cardiac conduction system) of the cardiac conduction system, through the pacing electrode (e.g., cathode) at the distal end 110 of the probe 110, to stimulate the cardiac conduction system.

Sensing can be conducted to detect the electrocardiogram of the heart or the electrical potential of the cardiac conduction system during the stimulation (e.g., response of the heart evoked by the pacing) during or after the pacing. In an embodiment, the sensing can be conducted via a separate sensing device (e.g., a device detecting body electrocardiogram of the heart, or the like). In another embodiment, the sensing can be conducted via a sensing electrode at the distal end 110 of the probe 110. An algorithm can be executed to determine whether the detected electrocardiogram of the stimulation during or after the pacing is a desired electrocardiogram. If yes, the location of the distal end 110 of the probe 110 is determined to be the desired location. If not, the distal end 110 of the probe 110 needs to be moved/adjusted, and the pacing and sensing sequence is to be conducted again to determine the desired location.

When the desired location is determined (and marked by the distal end 110 of the probe 110), the lead can be inserted through the orifice 154 extending from the proximal end 170 of the catheter 150 to the distal end 160 of the catheter 150. A distal end of the lead can be placed to the desired location. The catheter 150 and the probe 100 then can be removed.

It will be appreciated that positioning the catheter 150 against the septum can include one or more of the steps of pulling the first deflection wire 810 to deflect the distal end 160 of the catheter 150 (e.g., pulling the first deflection wire 810 to deflect the distal end of the catheter in a first plane, or pulling the first deflection wire 810 to deflect a tip 162 of the distal end 160 of the catheter 150), pulling the second deflection wire 820 to further deflect the distal end 160 of the catheter 150 (e.g., pulling the second deflection wire 820 to deflect the distal end 160 of the catheter 150 in a second plane perpendicular to the first plane, or pulling the second deflection wire 820 to deflect a location 164 of the distal end 160 of the catheter 150), and positioning a tip 162 of the distal end 160 of the catheter 150 to be perpendicular to an endocardial surface of the septum.

It will also be appreciated that an outer diameter of the probe 100 is much less than an outer diameter of a lead electrode (e.g., 3-5 French), by using the probe 100, embodiments disclosed herein can determine the desired location in the cardia conduction system by causing less trauma to the heart tissue. The probe can be placed on/against the surface of the septum or be inserted to the ventricular septum to locate a cardiac conduction system path-way such as the RBB or the LBB.

Figure 4A:
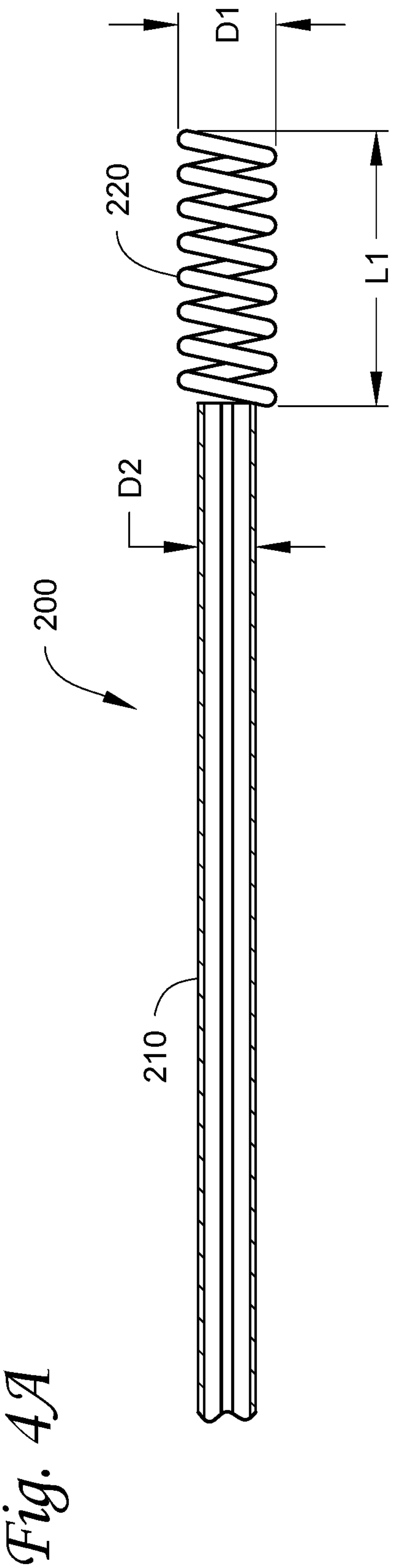
FIG. 4A is a perspective view of a lead, according to an embodiment.
Figure 4B:
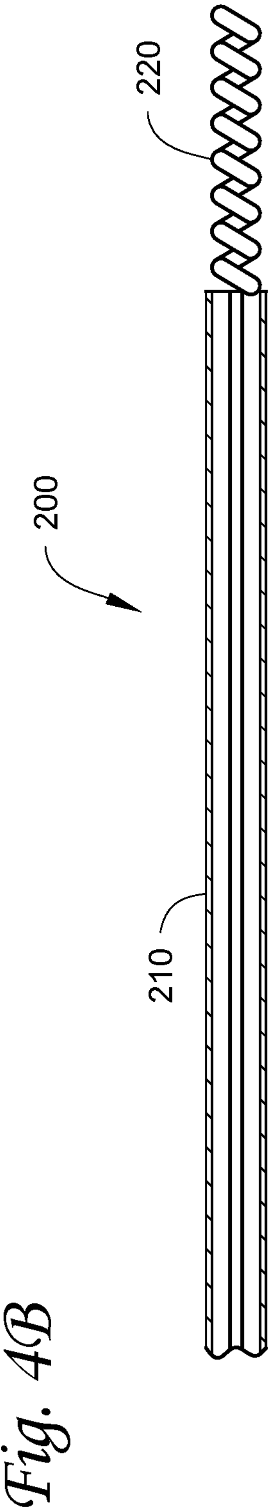
FIG. 4B is a perspective view of a lead, according to another embodiment.
Figure 4C:
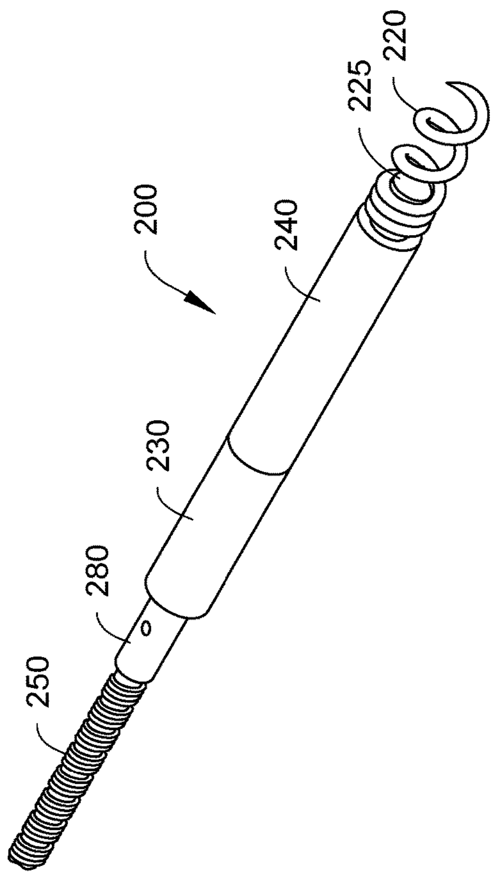
FIG. 4C is a perspective view of a lead, according to yet another embodiment.
Figure 4D:
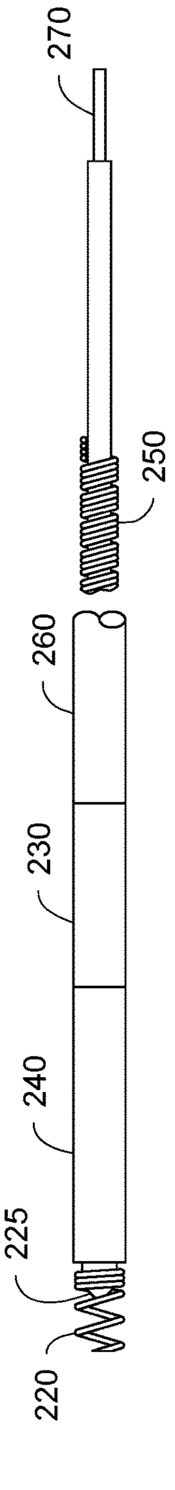
FIG. 4D is a side view of the lead of FIG. 4C, according to an embodiment.

FIG. 4A is a perspective view of a lead 200, according to an embodiment. FIG. 4B is a perspective view of a lead 200, according to another embodiment. FIG. 4C is a perspective view of a lead 200, according to yet another embodiment. FIG. 4D is a side view of the lead 200 of FIG. 4C, according to an embodiment.

The lead 200 includes a lead body 210 (to be described in more detail in FIGS. 7A-7E) and a distal end including a helix electrode 220. The proximal end of the lead is not shown.

As shown in FIG. 4A, the outer diameter D1 of the helix electrode 220 is greater than the outer diameter D2 of the lead body 210. As shown in FIG. 4B, the outer diameter D1 of the helix electrode 220 can be equal to the outer diameter D2 of the lead body 210.

As shown in FIG. 4C, the lead 200 includes a lead body (240, 230, 280, 250), which is the same as or similar to the lead body of FIGS. 7A-7E, unless explicitly specified otherwise. The lead 200 also includes a distal end having an electrode 220 (e.g., a helix electrode or the like). The lead body includes a non-conductive spacer 240 proximal to the helix electrode 220, an outer electrode 230 (e.g., a ring electrode disposed around the lead body made of titanium, platinum, platinum-iridium alloy, or the like, and coated for increased surface area) proximal to the spacer 240, an electrode coil 250 (e.g., the coil of the ring electrode) extends to the proximal end of the lead 200 and connects to a connector (not shown) at the proximal end of the lead body, and an inner electrode 280 (e.g., a coupler or the like) that connects the electrode coil 250 to the outer electrode 230. It will be appreciated that an insulation layer that covers the electrode coil 250 and the inner electrode 280 is cut away so that the electrode coil 250 and the inner electrode 280 are shown. In an embodiment, the insulation layer has the same material (e.g., polyurethane or the like) as the non-conductive spacer 240.

In an embodiment, the spacer 240 has a length ranges from at or about 4 millimeters to at or about 12 millimeters. The ring electrode 230 has a length ranges from at or about 1 millimeter to at or about 4 millimeters (e.g., to achieve high current density in pacing or the like). A diameter of the windings of the coil/wire of the helix electrode is at or about 0.25 millimeters. The helix electrode 220 includes a first portion extending distally from the lead body (e.g., from the spacer 240), and a second portion extending distally from the first portion. The helix electrode 220 also includes a core 225 (e.g., a linear core having a tapered tip that can drive the helix electrode 220 into the heart tissue easier). The core 225 of the helix electrode 220 is disposed inside and extended through an inner space of the first portion. The outer diameter of the linear core 225 (except the tapered tip) is or about the same as the inner diameter (e.g., at or about 1 millimeter, or ranges from at or about 0.5 millimeters to at or about 1.5 millimeters) of the first portion. The tapered tip of the core 225 extends into a portion of an inner space of the second portion of the helix electrode 220. In an embodiment, the length of the core (extending from the leady body) can range from at or about 0.5 millimeters or at or about 1 millimeter to at or about 2 millimeters. The length of the core can be less than a length of the helix electrode 220 (extending from the leady body). In another embodiment, the length of the core can be the same as or slightly longer than the length of the helix electrode 220. The spacing between the windings of the coil/wire of the second portion of the helix electrode 220 can be greater than the spacing between windings of the coil/wire of the first portion of the helix electrode 220. In an embodiment, the helix electrode 220 can have a length ranges from at or about 2.2 millimeters to at or about 2.6 millimeters, preferably at or about 2.4 millimeters, which is greater than a length of a conventional helix electrode of at or about 1.8 millimeters. In another embodiment, the helix electrode 220 can have a length of at or about 4 millimeters. In an embodiment, a proximal portion of the helix electrode 220 can be coated with non-conductive material. In another embodiment, the proximal portion of the helix electrode 220 is not coated with non-conductive material. In an embodiment, a surface of the core 225 can be threaded.

In an embodiment, the spacer 240 can be made with different length (at or about 4 mm, at or about 6 mm, at or about 8 mm, at or about 12 mm, or the like, to be suitable to capture both the LBB and the RBB with the helix and ring electrodes) to correspond to various thickness of the ventricular septum. In such embodiment, in operation, ultrasound or the like can be performed to measure the thickness of the ventricular septum and to determine and/or select the desired length of the spacer. In another embodiment, a length of the spacer 240 can vary (see e.g., 450 of FIGS. 7A-7E).

It will be appreciated that the length of the core can be critical to facilitate advancing the lead into the inter-ventricular septum. In an embodiment, the core being conductive can help increase the electrical surface area of the helix electrode. In another embodiment, the core being non-conductive can help reducing sensing and/or pacing noise. The outer diameter of the lead body can be critical to reduce trauma and/or facilitate deep-seating. The length of the helix electrode (and/or the length of the spacer, and/or the length of the ring electrode) can be critical to facilitate locating the LBB (or LBB area) and/or the RBB (or RBB area) for reliable sensing and/or pacing by any of the electrode(s) at or near the LBB (or LBB area) and/or the RBB (or RBB area).

FIG. 4D is a side view of the lead 200 of FIG. 4C, according to an embodiment. The lead of FIG. 4D is the same as or similar to the lead of FIG. 4C, unless explicitly specified otherwise. As shown in FIG. 4D, the lead 200 includes a lead body (240, 230, 260, 250, 270), which is the same as or similar to the lead body of FIGS. 7A-7E, unless explicitly specified otherwise. The lead body includes the insulation layer 260 (made of polyurethane or the like, which covers the inner electrode 280 of FIG. 4C). An inner wire 270 is disposed in an inner tube that is inserted in an inner space of the electrode coil 250. The inner wire 270 connects to the helix electrode 220 at the distal end of the lead 200 and to a connector (not shown) at the proximal end of the lead 200.

In an embodiment, an outer diameter of the lead body can be at or about 4.2 French or range from at or about 2.0 French to at or about 5.0 French. It will be appreciated that the core 225 can be either electrically conductive or non-conductive. Preferably, the core 225 is non-electrically conductive. In an embodiment, the core 225 can be made of metallic material (e.g., alloy or the like) coated with electrical insulation layer or can be made of polymer materials.

In an embodiment, an outer diameter of the lead body can be at or about or less than 5 French. The lead 200 can be bipolar with a distal helix electrode and a proximal ring electrode. The lead, the lead body, and/or the electrode(s) can be configured for elution of a compound such as a steroid, e.g., to suppress inflammatory response which may cause threshold rises typically associated with implanted pacing electrode(s). The core 225 (e.g., a cone-shaped component) can be incorporated within the helix electrode 220 to facilitate the "deep seating" of placing (e.g., screwing, etc.) the helix electrode and/or the ring electrode 230 inside the inter-ventricular septum. The core 225 is disposed within the helical space of helix electrode 220 and can be used for ease of advancing the lead into the inter-ventricular septum. The core 225 can be made of e.g., metallic material or any other suitable material. In an embodiment, the core 225 can be not electrical conducting (e.g., with surface coated with an electrical insulating material, a biocompatible polymer material, or the like). In an embodiment, the core 225 may not be coated so that it is electrically conductive. The ring electrode 230 can have a length of at or about 2 millimeters (e.g., to achieve high current density in pacing or the like). In an embodiment, the core can have a solid body. In another embodiment, the core 225 can have a hollow body (not shown) and be configured to include a steroid component/container inside the body of the core 225, with a porous surface (not shown, e.g., non-conductive, coated with non-conductive material) for steroid elution (e.g., elution of the steroid from the steroid component) into the surrounding heart tissue. In an embodiment, the hollow body of the core 225 can be the steroid container. In an embodiment, the lead 200 can be delivered transvenously using e.g., at or about or larger than 6 French inner diameter sheath or catheter, a guide wire, or a stylet. The inner diameter of the sheath or catheter can be critical to accommodate the size of the lead described herein.

Embodiments disclosed herein can provide increased pulling force (e.g., when the helix electrode is screwed into the ventricular septum) and better electrical performance than a conventional lead, and can facilitate ease of the lead 200 being deep seated (being inserted deep) into and can facilitate fixation of the lead onto the ventricular septum (e.g., the helix electrode being at or around the LBB inside the septum and the ring electrode 230 being at or around the RBB inside the septum). Embodiments disclosed herein can add surface area to the electrode (e.g., by having the core).

In an embodiment, a length L1 of the helix electrode 220 can be at or about four millimeters. In an embodiment, the helix electrode can be a single polar electrode. In another embodiment, the helix electrode can be a bipolar electrode. In an embodiment, the ring electrode 230 can be the same as 330 of FIG. 11. In an embodiment, the lead 200 can include another ring electrode (see 330 in FIG. 11), which can be disposed outside of the ventricular septum in the RV chamber proximal to the ring electrode 230 (which can be either disposed inside the ventricular septum or outside the ventricular septum).

It will be appreciated that compared with conventional RV or LV pacing, CSP requires the lead being "deep" seated into the ventricular septum (inserted inside the ventricular septum in a much greater distance, e.g., the lead body 210 being partially inside the tissue of ventricular septum) of the cardiac conduction system (e.g., to reach the LBB), embodiments disclosed herein can provide an electrode that is longer (e.g., at or about 4 mm) than conventional electrode (e.g., a little bit less than 2 mm), and/or is or about as large as or larger than the diameter of the lead body 210 to facilitate deep seating. Testing shows that a lead with the helix and the core design can be easier to deep seat into the ventricular septum or myocardial tissue.

Figure 5:
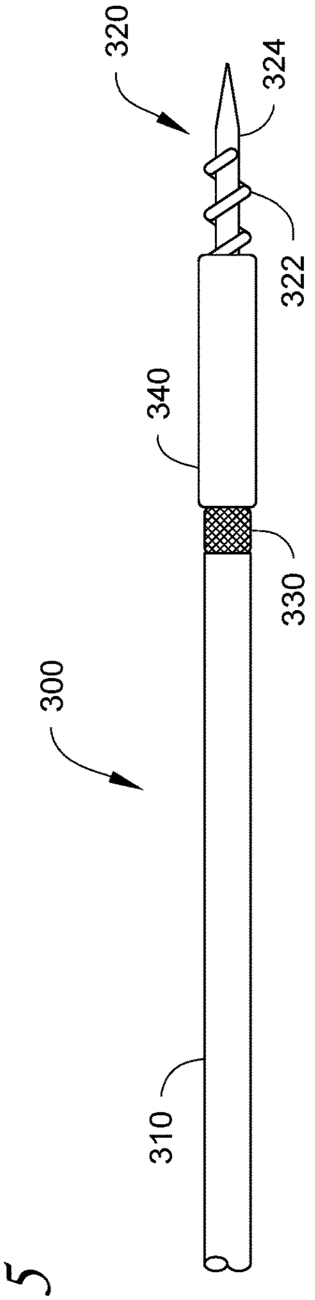
FIG. 5 is a perspective view of a lead, according to yet another embodiment.

FIG. 5 is a perspective view of a lead 300, according to yet another embodiment. The lead 300 includes a lead body 310 (to be described in more detail in in FIGS. 7A-7E) and a distal end 320 including a linear electrode 324 having a tapered tip and a rod integral to the tapered tip. The proximal end of the lead is not shown. A helix wire 322 is wrapped around (and in contact with) the rod of the linear electrode 324. In an embodiment, the helix wire 322 is integral to the rod of the linear electrode 324, and the helix wire 322 and the linear electrode 324 form an auger (helix auger) electrode (322, 324).

In an embodiment, a ring electrode 330 proximal to the auger electrode can be disposed on and around the lead body 310. A non-conductive spacer 340 can be disposed on the lead body 310 between the ring electrode 330 and the auger electrode. As shown in FIG. 5, the outer diameter of the spacer 340 is greater than the outer diameter of the ring electrode 330 and/or the lead body 310. In such embodiment, the spacer 340 can serve as a stopper to prevent the distal end 320 from being advancing further into the septum. In another embodiment, the outer diameter of the spacer 340 can be the same as the outer diameter of the ring electrode 330 and/or the lead body 310 to facilitate smooth movement of the lead 300 and deep-seating. The linear electrode 324 and/or the helix wire 322 can be made of metal or any suitable material.

It will be appreciated that the tapered or pointed tip of the auger electrode (322, 324) can be configured to penetrate the heart tissue (e.g., the ventricular septum), and when the helix wire 322 touches the tissue, the lead can be turned (e.g., in a clockwise or counterclockwise direction) to pose/dispose the auger electrode (322, 324) into the heart tissue. Embodiments disclosed herein can help with deep seating the electrode, and/or to overcome the difficulties of conventional lead design during implantation. For example, when there is only helix electrode 322 on the distal tip (without the rod and/or the tip of 324), when fixating or advancing the helix electrode into the myocardial tissue, the helix electrode might be caught in a piece of fiber tissue or get entangled with the heart tissue which may prevent the advancement of the lead into the myocardial tissue.

Figure 6:
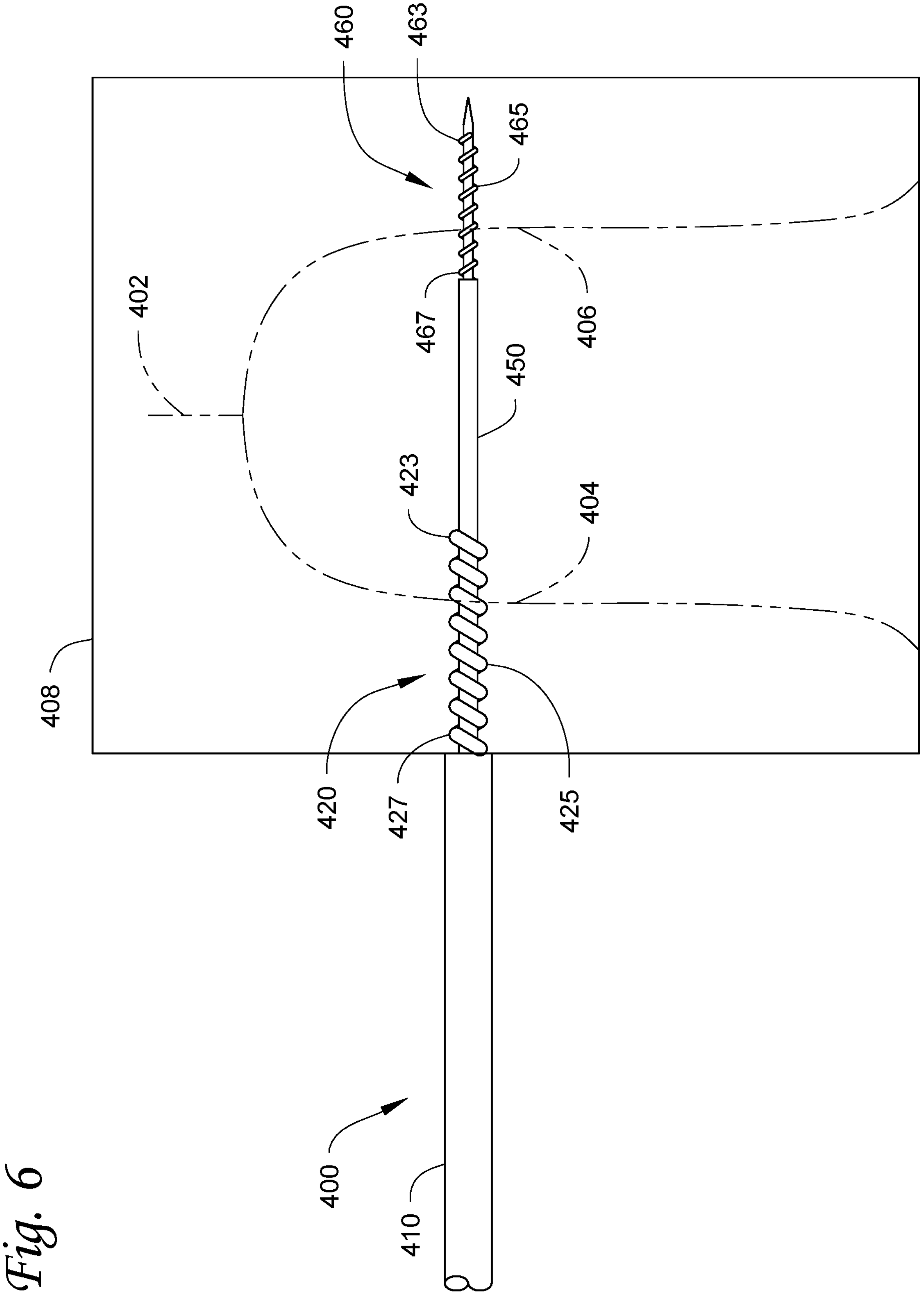
FIG. 6 is a perspective view of a lead being inserted in the ventricular septum, according to an embodiment.

FIG. 6 is a perspective view of a lead 400 being inserted in the ventricular septum 408 of the cardiac conduction system, according to an embodiment. The cardiac conduction system includes conduction pathways including the His-bundle 402, the RBB 404, the LBB 406 and both RBB and LBB.

As shown in FIG. 6, the lead 400 includes a lead body 410 (to be described in more detail in FIGS. 7A-7E) and a distal end including a first electrode 460 having a tapered tip and a rod integral to the tapered tip, a spacer 450 (non-conductive, e.g., coated with electrical insulation layer) connected to the first electrode 460, and a second electrode 420 fixed to the lead body 410. In an embodiment, the first electrode 460 can include a proximal coated (with non-conductive material, for electrical insulation) region and an uncoated tip (which serve as electrode(s)). The proximal end of the lead is not shown.

In an embodiment, the first electrode 460 can be a linear electrode. In another embodiment, the first electrode 460 can be an auger electrode such as a helix auger where an outer surface of a rod and/or a tip of a linear electrode is threaded for deep seating the first electrode 460. In an embodiment, the second electrode 420 is a helix electrode. In an embodiment, the spacer 450 can be fixed (e.g., a distance between the first electrode 460 and the second electrode 420 can be fixed). In another embodiment, the spacer 450 can be adjustable to distally extend or proximally retract the first electrode 460, so that the spacing between the first electrode 460 and the second electrode 420 can vary (to provide variable spacing between the first electrode 460 and the second electrode 420). A length of the spacer 450 (i.e., a distance between the first electrode 460 and the second electrode 420 when the lead is fully deployed) can be at or about four millimeters.

In an embodiment, the first electrode 460 can be a single polar electrode (e.g., cathode). In an embodiment, the first electrode 460 can be a bipolar electrode including e.g., a distal cathode 463, a non-conductive middle portion 465, and a proximal anode 467. The first electrode 460 can have a length of at or about four millimeters. The distal cathode 463 of the first electrode 460 can have a length of at or about one millimeter, the non-conductive middle portion 465 can have a length of at or about two millimeters, and the proximal anode 467 can have a length of at or about one millimeter.

In an embodiment, the second electrode 420 can be a single polar electrode (e.g., anode). In an embodiment, the second electrode 420 can be a bipolar electrode including e.g., a distal cathode 423, a non-conductive middle portion 425, and a proximal anode 427. The second electrode 420 can have a length of at or about four millimeters. The distal cathode 423 of the second electrode 420 can have a length of at or about one millimeter, the non-conductive middle portion 425 can have a length of at or about two millimeters, and the proximal anode 427 can have a length of at or about one millimeter.

In another embodiment, the electrode 420 can be a bipolar electrode including e.g., a distal portion and a proximal portion. The distal portion of the electrode 420 can be non-conductive (e.g., used as fixation) and the proximal portion can be conductive (e.g., used as electrode). In such embodiment, the electrode 420 can have a length of at or about four millimeters, the distal portion of the electrode 420 can have a length of at or about two millimeters, and the proximal portion can have a length of at or about two millimeters.

In an embodiment, an outer diameter of the first electrode 460 ranges from at or about three French to at or about five French. In an embodiment, the lead 400 can include a ring electrode (see e.g., 330 of FIG. 5).

As shown in FIG. 6, the second electrode 420 is disposed/placed at or near the RBB 404 (e.g., for RBBP) inside the ventricular septum 408, the first electrode 460 is disposed/placed at or near the LBB 406 (e.g., for LBBP) inside the ventricular septum 408. It will be appreciated that optimal electrical performance can be achieved when the electrode(s) are disposed/placed at the desired location (e.g., at or near the conduction pathway(s) that electrical impulses (e.g., a burst of energy) are to be delivered or sensing signals are to be detected). It will also be appreciated that a thickness of the ventricular septum 408 (e.g., in a direction from the left to the right) can be at or about 13 millimeters. It will further be appreciated that the thickness of the ventricular septum 408 can vary from person to person. For example, the older the person is, typically the thicker the ventricular septum 408 is. It will also be appreciated that the closer the electrode of the lead is to the RBB/LBB, the lower the voltage it may take to provide cardiac conduction system stimulations, and thus the lead needs to go deeper to the ventricular septum 408.

In an embodiment, the spacer 450 extends from a distal tip of the lead body 410. An outer diameter of the spacer 450 can be smaller than an inner diameter of the second electrode 420 (the helix electrode), such that the spacer and the second electrode 420 are co-axial, and/or that the spacer 450 is disposed in the helical space of the second electrode 420. In an embodiment, the second electrode 420 can wrap around (and in contact with) the spacer 450.

Figure 7A:
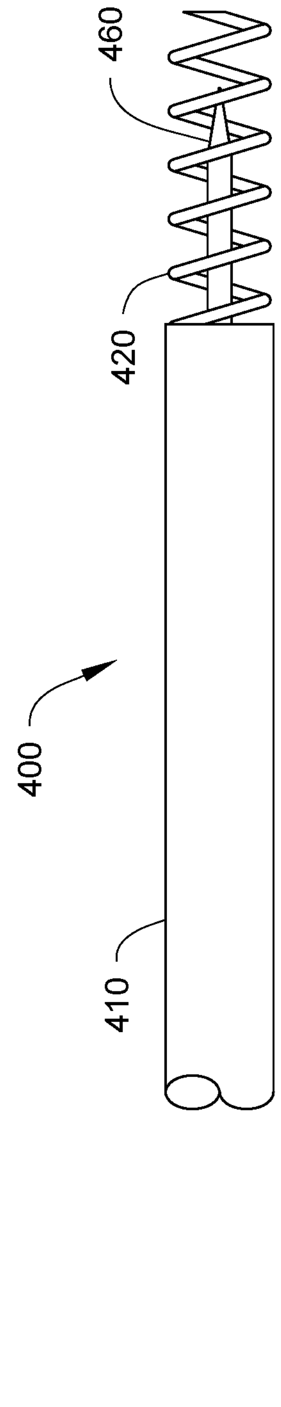
FIG. 7A is a perspective view of a lead in a retracted state, according to an embodiment.
Figure 7B:
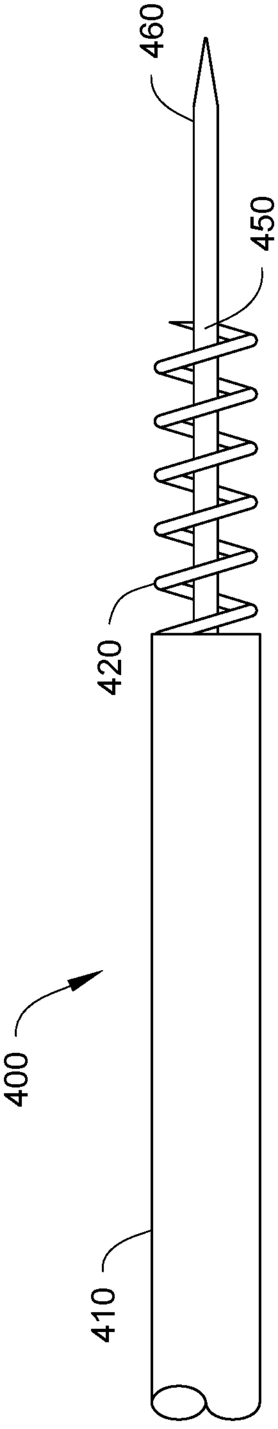
FIG. 7B is the lead of FIG. 7A in an extended state, according to an embodiment.
Figures 7C, 7D, 7E:
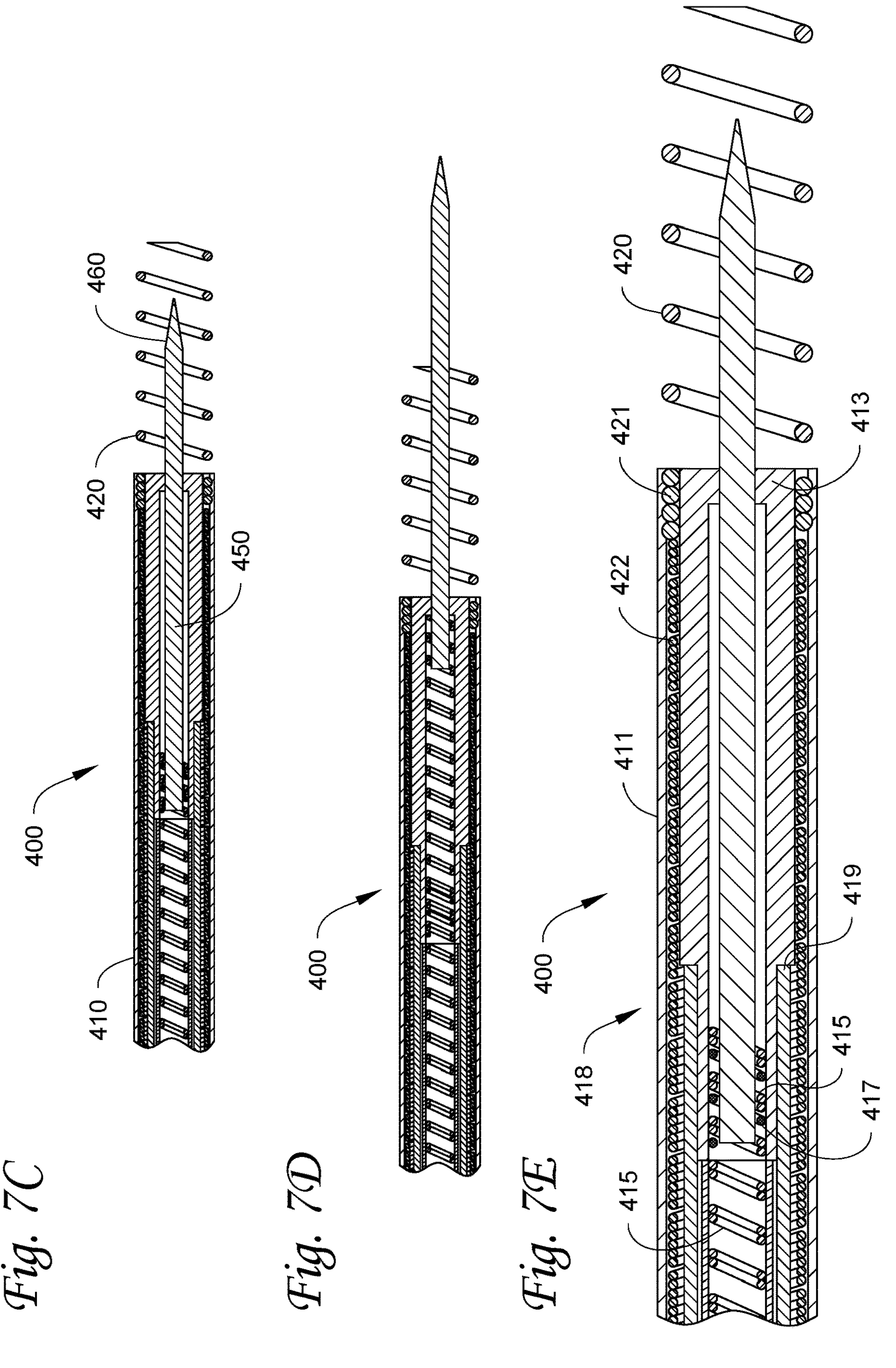
FIG. 7C is a cross-sectional view of a lead in a retracted state, according to an embodiment.
FIG. 7D is the lead of FIG. 7C in an extended state, according to an embodiment.
FIG. 7E is an enlarged view of FIG. 7C, according to an embodiment.

FIG. 7A is a perspective view of a lead 400 in a retracted state, according to an embodiment. FIG. 7B is the lead 400 of FIG. 7A in an extended state, according to an embodiment. FIG. 7C is a cross-sectional view of a lead 400 in a retracted state, according to an embodiment. FIG. 7D is the lead 400 of FIG. 7C in an extended state, according to an embodiment. FIG. 7E is an enlarged view of FIG. 7C, according to an embodiment.

As shown in FIGS. 7A-7E, the lead 400 includes a lead body 410 and a distal end including a first electrode 460 having a tapered tip and a rod integral to the tapered tip, a spacer 450 connected to the first electrode 460, and a second electrode 420 fixed to the lead body 410. The proximal end of the lead is not shown. In an embodiment, the lead of FIGS. 7A-7E can be the lead of FIG. 6.

The lead body 410 includes an outer layer 411 (that is an insulation layer) and an outer coil 422 having windings spaced close to each other. The windings of the outer coil 422 clings to an inner surface of the outer layer 411. The lead body 410 has a distal end 418. The outer coil 422 extends from a proximal end of the lead body 410 to a location close to a distal tip of the distal end 418 of lead body 410. Inside the outer layer 411 near the distal tip of the distal end 418, the second electrode 420 has windings 421 spaced close to each other (so that there can be more wires inside the lead body to keep the helix electrode in place). The windings of the second electrode 420 extends outside of the lead body 410, and (the portion of) the windings of the second electrode 420 that is outside of the lead body 410 are spaced apart from each other. In an embodiment, a diameter of the windings of the second electrode 420 is larger than a diameter of the windings of the outer coil 422. In an embodiment, the outer coil 422 (electrically) connects to the second electrode 420 so that electrical impulses (e.g., a burst of energy) can be delivered via the outer coil 422 to the second electrode 420 (or sensing signals can be detected at the second electrode 420 and carried over to a device through the outer coil 422).

A middle layer 419 extends from a proximal end of the lead body 410 to a portion of the distal end 418 of the lead body 410. The middle layer 419 clings to an inner surface of the outer coil 422. A housing 413 is disposed inside the outer coil 422 and the windings 421 of the second electrode 420 inside the lead body 410. A proximal portion of the housing 413 is disposed between the middle layer 419 and an inner coil 415. A middle portion of the housing 413 is disposed between the outer coil 422 (and the windings 421) and the inner coil 415. A distal portion of the housing 413 is disposed between the windings 421 and the spacer 450 (or the rod of the first electrode 460). In an embodiment, the housing 413 is made of plastic.

The inner coil 415 extends from a proximal end of the lead body 410 to a location close to the distal tip of the distal end 418 of lead body 410. In an embodiment, the inner coil 415 (electrically) connects to the first electrode 460 so that electrical impulses (e.g., a burst of energy) can be delivered via the inner coil 415 to the first electrode 460 (or sensing signals can be detected at the first electrode 460 and carried over to a device through the inner coil 415). The inner coil 415 clings to an inner surface of the middle layer 419 and an inner surface of a portion of the housing 413. At the proximal portion of the housing 413 and between windings of inner coil 415, a plurality of drive components (drive "tooth") is disposed at, fixed to, and clings to an inner surface of the proximal portion of the housing 413. The drive components are configured to cause the inner coil 415 to extend distally or retract proximally the spacer 450 (and the first electrode 460 that connects to the spacer 450). In an embodiment, an IS-1 pin (not shown) or any suitable control mechanism at the proximal end of the lead 400 can be rotated to drive the inner coil 415 to extend distally or retract proximally the spacer 450 (and the first electrode 460 that connects to the spacer 450).

In an embodiment, the spacer 450 can be integral to the first electrode 460 as an electrode (e.g., single polar or bipolar, made of metal or the like). In such embodiment, the spacer 450 portion of the electrode can be coated (to be non-conductive, e.g., with an electrical insulation layer), and the first electrode 460 portion or a distal tip portion of the electrode is not coated for stimulation delivery (pacing, e.g., delivering electrical impulses) and/or sensing. Since the second electrode 420 is fixed to the lead body (e.g., via windings 421), rotating the lead 400 or the lead body 410 can extend distally or retract proximally the entire lead 400 (and therefore the second electrode 420 to engage with the heart tissue or retract from the heart tissue).

The spacer 450 and the first electrode 460 extends through a cavity inside the housing 413, through a space inside the outer coil 422, and through a space inside the second electrode 420. It will be appreciated that the phrase "retracted state" of the lead may refer to a state of the lead where the spacer 450 and the first electrode 460 are fully or partially retracted proximally (e.g., a distal end of the first electrode 460 is proximal to a distal end of the second electrode 420). The phrase "extended state" of the lead may refer to a state of the lead where the spacer 450 and the first electrode 460 are fully or partially extended distally (e.g., a distal end of the first electrode 460 is distal to a distal end of the second electrode 420).

In an embodiment, an outer diameter of the first electrode 460 (the linear electrode) can be smaller than an inner diameter of the second electrode 420 (the helix electrode), such that the first electrode 460 and the second electrode 420 are co-axial, and/or that the first electrode 460 is disposed in the helical space of the second electrode 420.

Figure 8A:
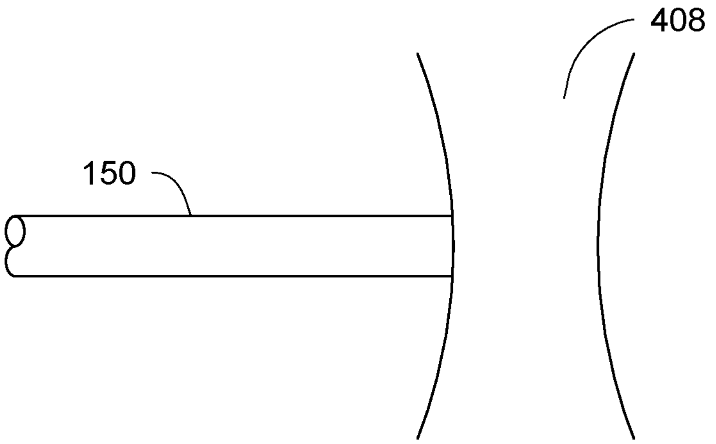
FIGS. 8A-8C illustrate a lead implant procedure, according to an embodiment.
Figure 8B:
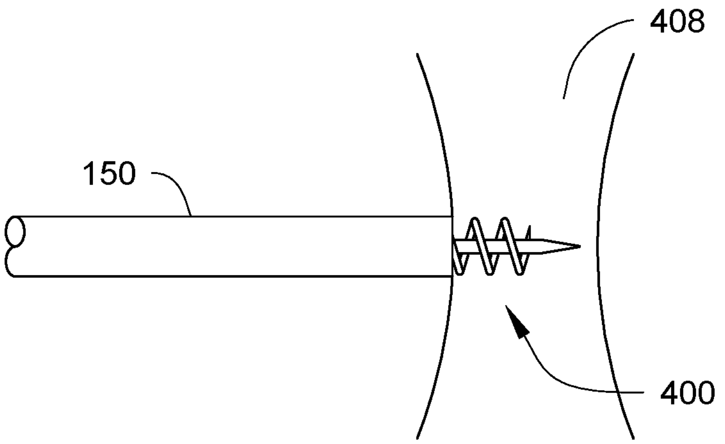
Figure 8C:
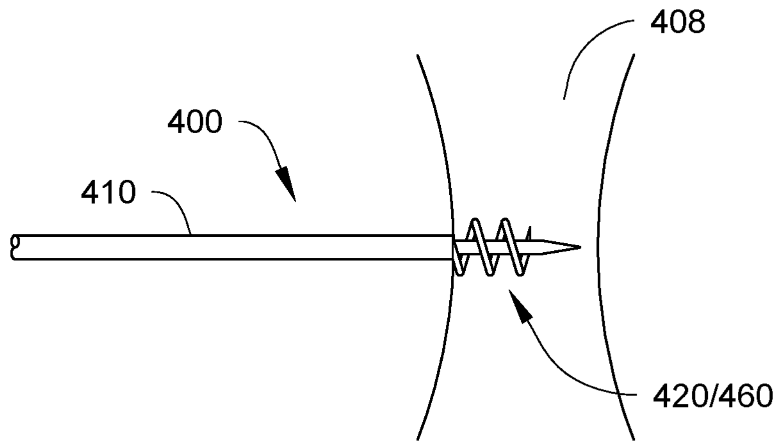

FIGS. 8A-8C illustrated a lead implant procedure, according to an embodiment. FIGS. 8D-8G illustrated a lead implant procedure, according to another embodiment.

Figure 8D:
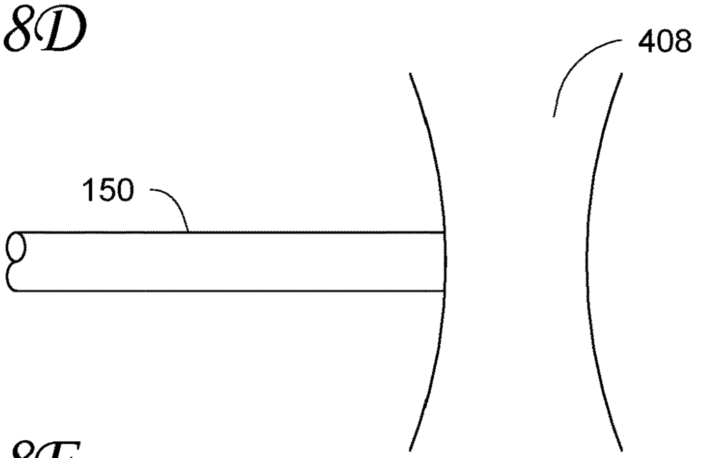
FIGS. 8D-8G illustrate a lead implant procedure, according to another embodiment.

A method of implanting a lead for cardiac conduction system using a catheter system can include one or more of the following steps. As illustrated in FIG. 8A or FIG. 8D, the method includes inserting a catheter 150 to reach the ventricular septum 408 of the cardiac conduction system. The method also includes positioning the catheter 150 against the ventricular septum 408. See e.g., the description for FIGS. 1-3 regarding the steps of positioning the catheter 150 against the ventricular septum 408 (e.g., deflecting the catheter 150, aligning a tip 162 of the distal end 160 of the catheter 150 to be perpendicular to an endocardial surface of the ventricular septum 408, pacing and/or sensing to determine a desired location, etc.).

Figure 8E:
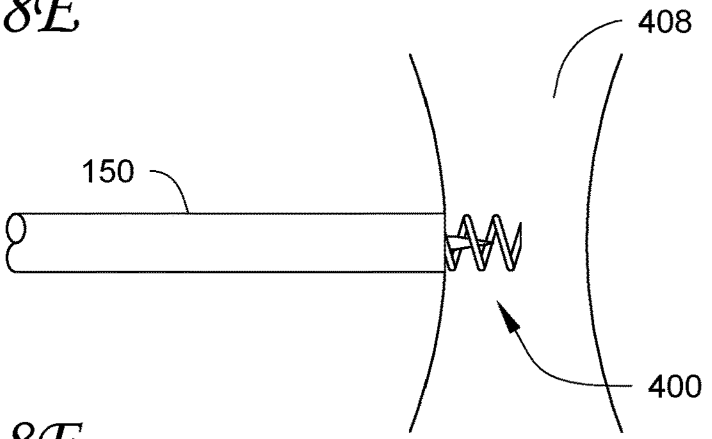

As illustrated in FIG. 8B or FIG. 8E, the method includes inserting the lead (e.g., 400) through an orifice 154 of the catheter 150 extending from a distal end of the catheter 150 to a proximal end of the catheter 150, to the desired location of the ventricular septum 408. It will be appreciated that the lead can be any lead described herein and can include any features of the lead described herein. The method also includes rotating the lead 400 or a lead body 410 of the lead 400 to engage a helix electrode of the lead 400 to the ventricular septum 408 (e.g., so that the electrode(s) of the lead 400 reach the respective conduction pathway(s) (e.g., His-bundle, RBB, LBB, etc.) of the cardiac conduction system).

Figure 8F:
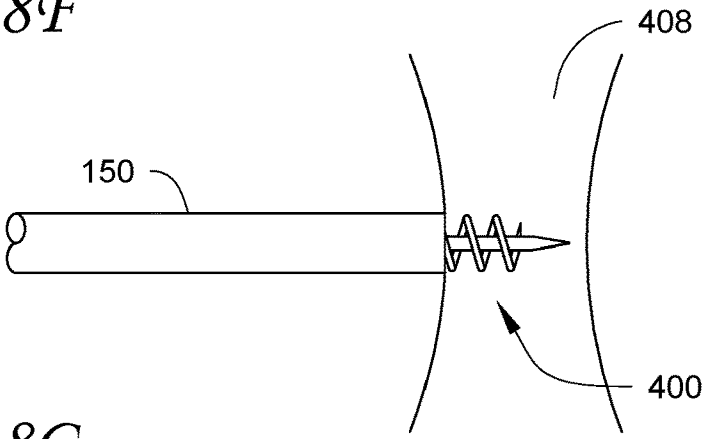
Figure 8G:
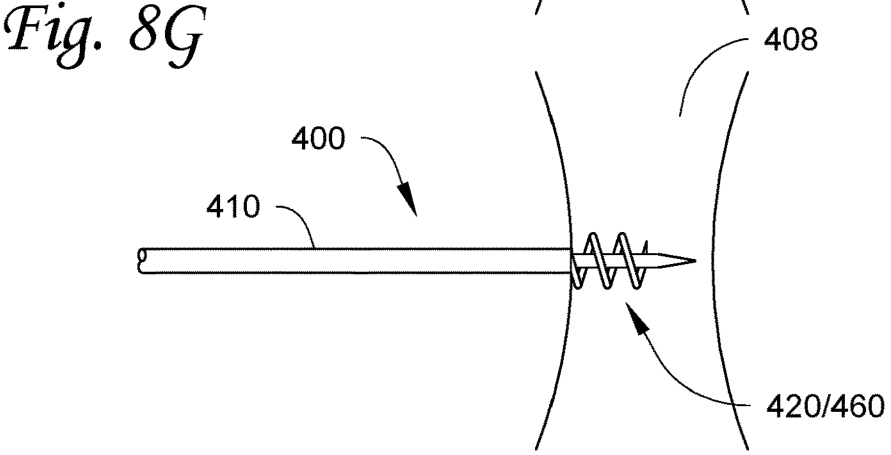

As illustrated in FIG. 8C or FIG. 8G, the method includes removing the catheter 150 so that the lead 400 is left in place after implanting the lead 400. In an embodiment, the catheter 150 can be slit (peeled away) to be removed. In another embodiment, the catheter 150 can be removed without being slit or peeled away.

As illustrated in FIG. 8B or FIG. 8F, the method includes partially engaging a linear electrode 460 of the lead 400 to the ventricular septum 408. The method further includes rotating a pin (e.g., an IS-1 pin or the like) or any suitable control mechanism at the proximal end of the lead 400 to extend and deploy the linear electrode 460 of the lead 400 into the ventricular septum (e.g., so that the electrode(s) of the lead 400 reach the respective conduction pathway(s) (e.g., His-bundle, RBB, LBB, etc.) of the cardiac conduction system).

Figure 9:
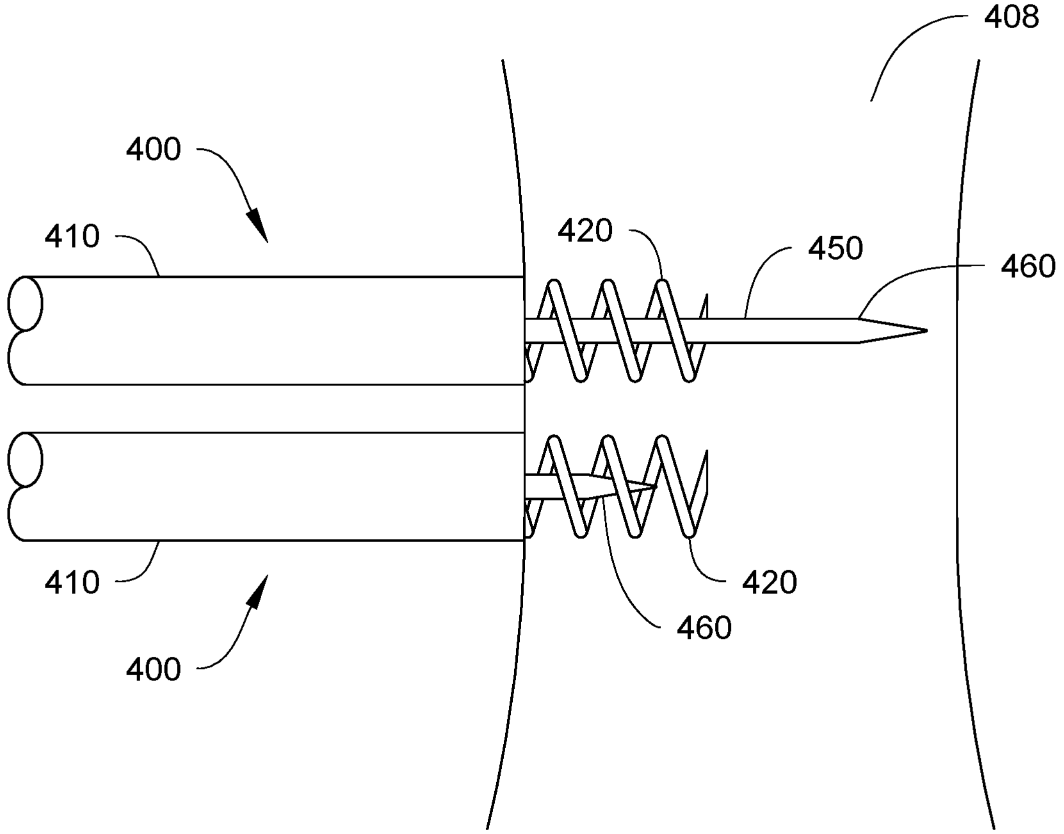
FIG. 9 illustrates a lead implant procedure, according to an embodiment.

FIG. 9 illustrates a lead implant procedure, according to an embodiment. A method of implanting a lead for cardiac conduction system using a catheter system can include one or more of the following steps. In addition to other steps described herein, the method includes rotating a pin (e.g., an IS-1 pin or the like) or any suitable control mechanism at the proximal end of the lead 400 to extend and deploy (or retract) the linear electrode 460 of the lead 400 into (or from) the ventricular septum. As illustrated in the upper portion of FIG. 9, the method also includes rotating the lead 400 or the lead body 410 to engage the helix electrode 420 of the lead 400 to the ventricular septum 408 (e.g., to reach at or near the RBB). The method further includes rotating the pin (e.g., an IS-1 pin or the like) or any suitable control mechanism at the proximal end of the lead 400 to extend the linear electrode 460 of the lead 400 into the ventricular septum (e.g., to reach at or near the LBB).

As illustrated in the lower portion of FIG. 9, the method can optionally include rotating (in an opposite direction to the extending operation) the pin (e.g., an IS-1 pin or the like) or any suitable control mechanism at the proximal end of the lead 400 to retract the linear electrode 460 of the lead 400 from (e.g., the LBB of or from other location of) the ventricular septum (e.g., to reach at or near the RBB; or in another embodiment, to reach at or near the LBB).

Figure 10:
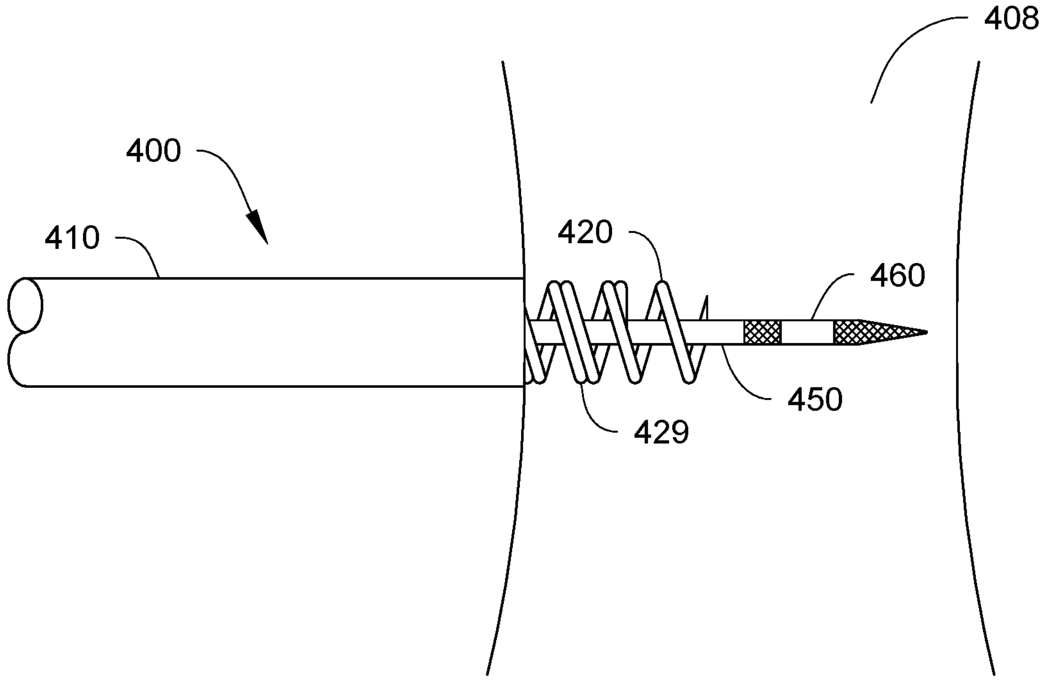
FIG. 10 is a perspective view of a lead being inserted in the ventricular septum, according to an embodiment.

FIG. 10 is a perspective view of a lead 400 being inserted in the ventricular septum 408, according to an embodiment. The lead 400 includes a lead body 410, a distal end, and a proximal end. The distal end includes a linear electrode 460 having a tapered tip and a rod integral to the tapered tip, a spacer connects to the linear electrode 460, and a first helix electrode 420 fixed to the lead body 410. The proximal end of the lead 400 is not shown. The distal end of the lead 400 also includes a second helix electrode 429 fixed to the lead body 410. A coil of the first helix electrode 420 and a coil of the second helix electrode 429 extend distally from the lead body 410 and wind alongside with each other. The coil of the first helix electrode 420 extends further distally than the coil of the second helix electrode 429. It will be appreciated that dual helixes can facilitate easy deep seating of the lead 400. It will be appreciated that the linear electrode 460 can be optional.

In an embodiment, the linear electrode 460 can be a bipolar electrode including a distal cathode, a non-conductive middle portion, and a proximal anode. In an embodiment, the first helix electrode 420 can be cathode and the second helix electrode 429 can be anode. In an embodiment, the spacer 450 and the linear electrode 460 can be optional. In such embodiment, the distal end of the lead 400 only includes two helix electrodes (420, 429).

In an embodiment, a portion of the first helix electrode 420 is insulated and is not electrically conductive. In an embodiment, the first helix electrode 420 and/or the second helix electrode 429 can be configured for elution of a compound such as a steroid. In an embodiment, the first helix electrode 420 and/or the second helix electrode 429 can be configured as a pacing electrode and/or a sensing electrode. In an embodiment, a portion of the first helix electrode 420 and/or a portion of the second helix electrode 429 can be insulated and not electrically conductive. In an embodiment, the lead 400 can further include a drug collar (not shown), for example a drug collar configured to release a steroid, at a lead body 410 distal tip proximal to the first helix electrode 420 and/or the second helix electrode 429.

Figure 11:
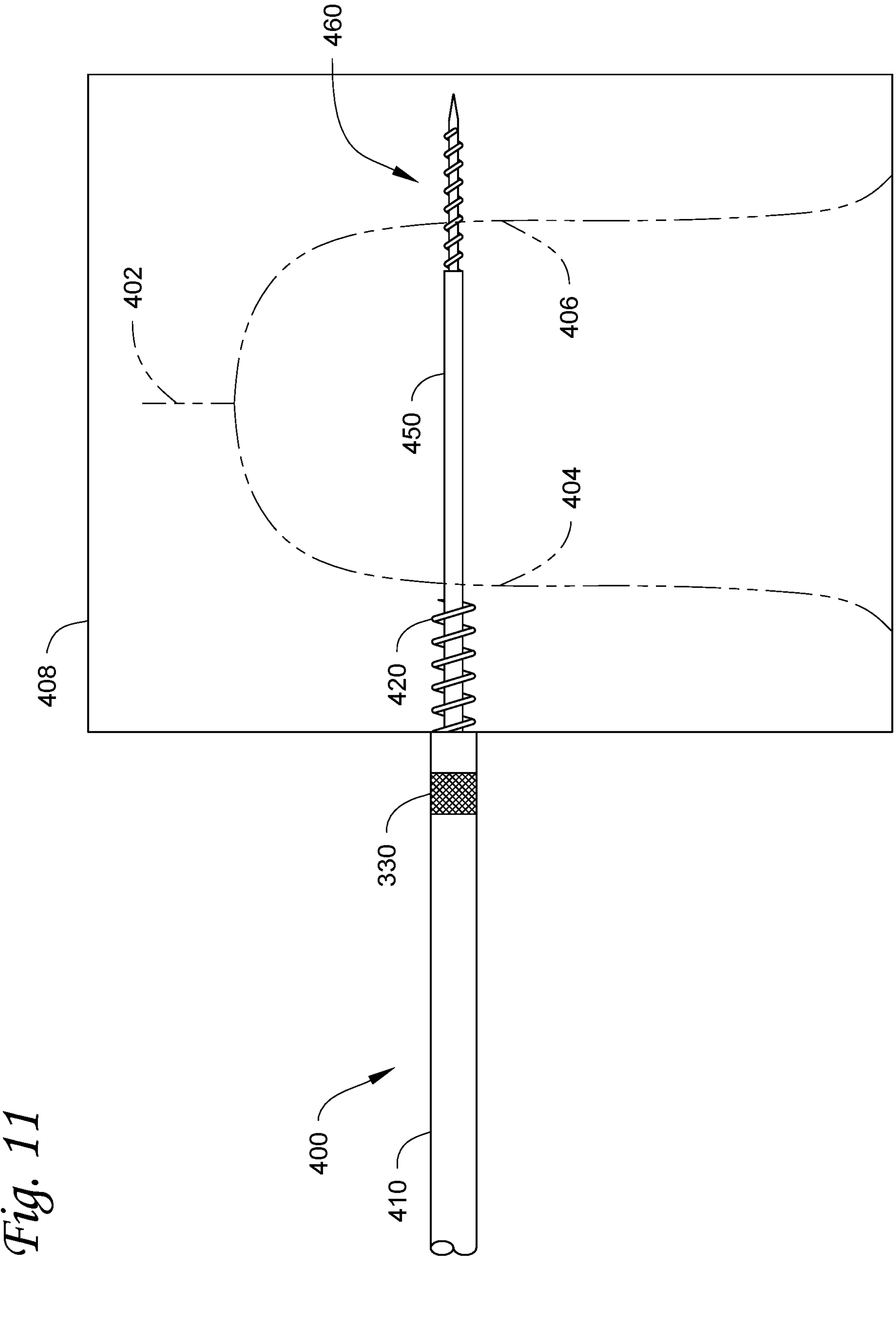
FIG. 11 is a perspective view of a lead being inserted in the ventricular septum, according to another embodiment.

FIG. 11 is a perspective view of a lead 400 being inserted in the ventricular septum 408, according to another embodiment. It will be appreciated that the lead of FIG. 11 can be the same as or similar to the lead of FIG. 6, unless explicitly specified otherwise. As shown in FIG. 11, the lead 400 includes a ring electrode 330 disposed around the lead body 410 proximal to the helix electrode 420. It will be appreciated that the ring electrode 330 of FIG. 11 can be the same as or similar to the ring electrode of FIG. 5, unless explicitly specified otherwise. The ring electrode 330 can be disposed outside (e.g., in contact with, or separate from) the ventricular septum 408 (e.g., in the right ventricle). In another embodiment, the ring electrode 330 can be disposed inside the ventricular septum 408.

Figure 12:
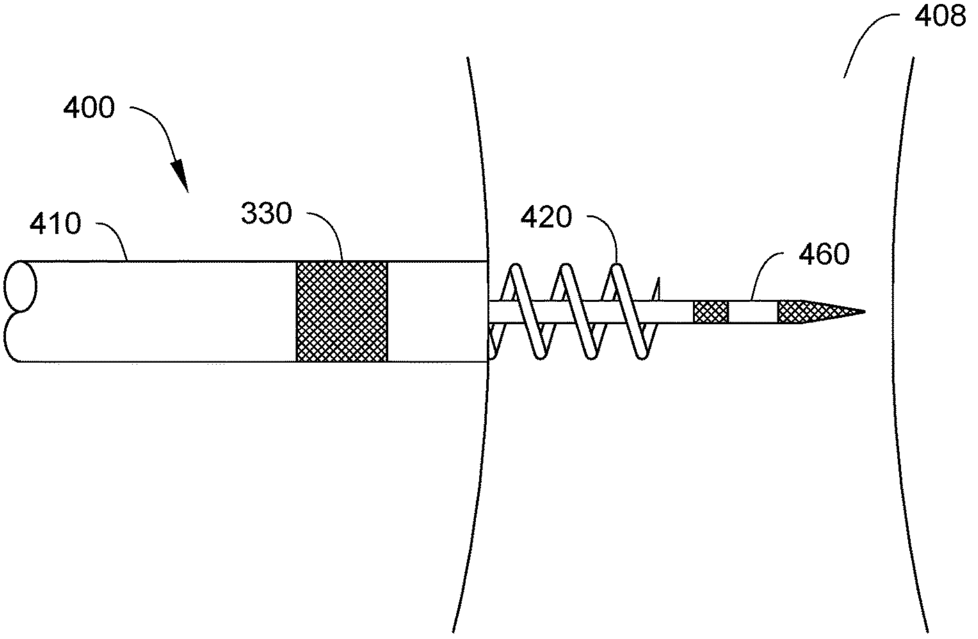
FIG. 12 is a perspective view of a lead being inserted in the ventricular septum, according to yet another embodiment.

FIG. 12 is a perspective view of a lead 400 being inserted in the ventricular septum 408, according to yet another embodiment. It will be appreciated that the lead of FIG. 12 can be the same as or similar to the lead of FIG. 10, unless explicitly specified otherwise. As shown in FIG. 12, the lead 400 includes a ring electrode 330 disposed around the lead body 410 proximal to the helix electrode 420. There is no electrode 429 in FIG. 12.

Figure 13:
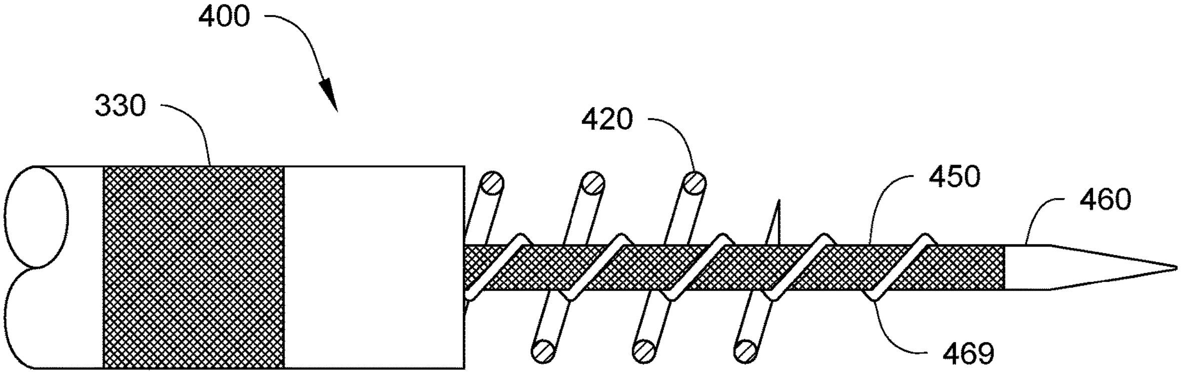
FIG. 13 is a cross-sectional view of a lead 400, according to an embodiment.

FIG. 13 is a cross-sectional view of a lead 400, according to an embodiment. It will be appreciated that the lead of FIG. 13 can be the same as or similar to the lead of FIG. 12, unless explicitly specified otherwise. As shown in FIG. 13, the spacer 450 includes an insulation layer covered around the spacer 450. The lead 400 also includes a second helix electrode 469 extends from the lead body and is winded on and/or over the insulation layer of the spacer 450. The second helix electrode 469 has an outer diameter smaller than an outer diameter of the first helix electrode 420.

In an embodiment, the linear electrode 460 can be cathode. The second helix electrode 469 can be anode. The first helix electrode 420 can be cathode. The ring electrode 330 can be anode.

Figure 14:
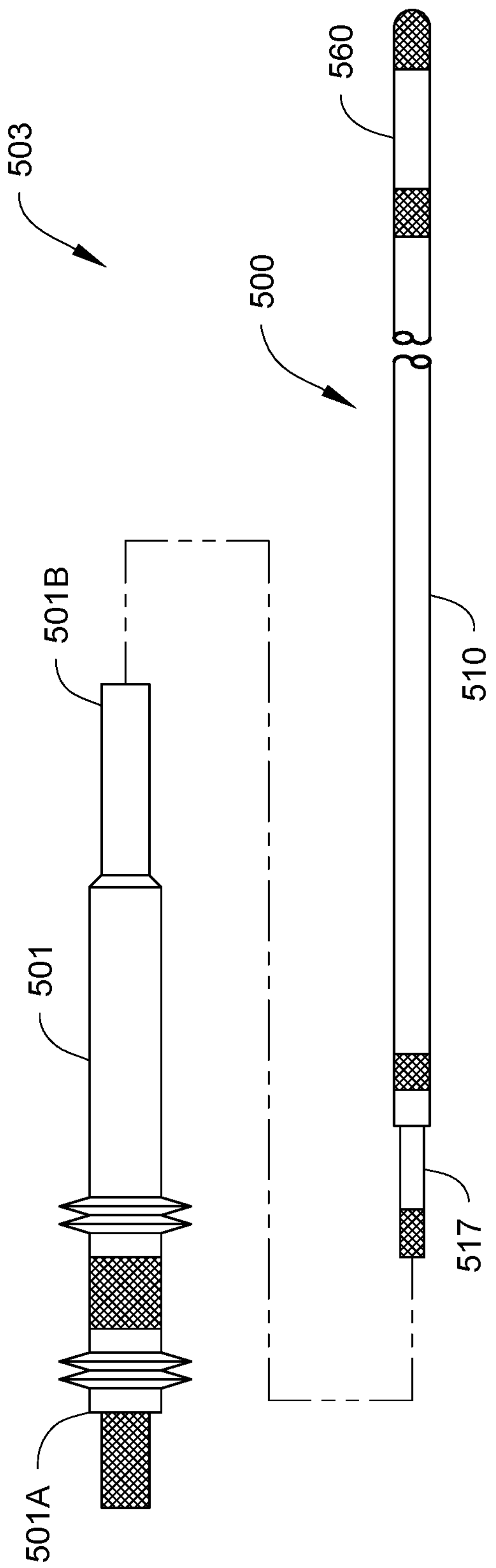
FIG. 14 is a perspective view of a lead assembly, according to an embodiment.

FIG. 14 is a perspective view of a lead assembly 503 for cardiac conduction system, according to an embodiment. The lead assembly 503 includes a lead 500 having a lead body 510, a distal end, and a proximal end 517. The lead assembly 503 also includes a connector 501 separate from the lead 500. An outer diameter of the lead body 510 is equal to or greater than an outer diameter of the proximal end 517. The outer diameter of the lead body 510 is equal to or greater than an outer diameter of the distal end. In an embodiment, the outer diameter of the lead body 510 is at or about three French. It will be appreciated that a small diameter (e.g., at or about three French) lead body can create less stress in heart tissue. The softer, the more flexible of the proximal end of the lead body, the less force needs to be put and the lead is less likely to be damaged, and such lead can minimize the trauma to the heart tissue and have a stable electrical performance.

The proximal end 517 is configured to connect to a first end 501B of the connector 501. A second end 501A of the connector 501 is configured to connect to a header of an implantable pulse generator (not shown). In an embodiment, the second end 501A of the connector 501 is an IS-1, IS-4, or DF-4 connector. Embodiments disclosed herein can help to remove the catheter without slitting the catheter (e.g., by using a detachable upsizing connector 501). The catheter can be removed by slipping over a small diameter proximal end of the lead. Embodiments disclosed herein also use an adaptor (the connector 501) to upsize the diameter of the lead to a standard size (IS/DF). The connector 501 is an upsizing connector (that increases the size of the lead to a standard size) that contains internal seals and/or contacts for sealed connection to the lead 500. In an embodiment, the lead body 510 has a uniform diameter (e.g., at or about three French) that can allow removal of catheter without slitting it. It will be appreciated that slitting the catheter may dislodge the lead, which is not desired.

In an embodiment, the distal end of the lead 500 includes a linear electrode 560 having a rod and a tapered or round tip. The linear electrode 560 can include a distal cathode, a non-conductive middle portion, and a proximal anode.

Figure 15:
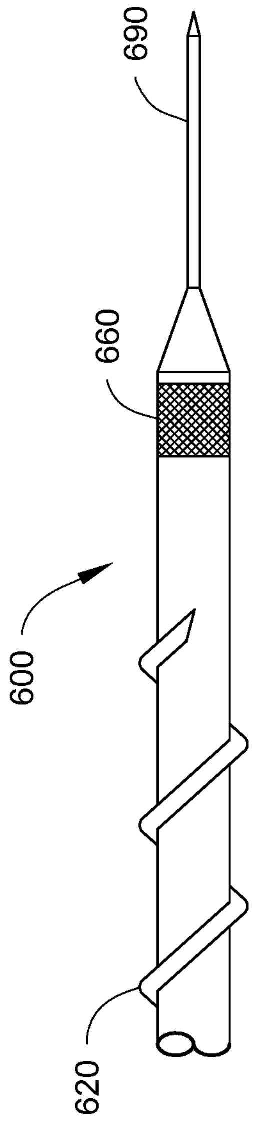
FIG. 15 is a perspective view of a lead with a wire, according to an embodiment.

FIG. 15 is a perspective view of a lead 600 with a wire or needle 690, according to an embodiment. The wire 690 can be a guide wire (configured to be deployed through a lumen of a catheter), a stylet wire (e.g., configured to be deployed through a lumen of the lead 600), or the like. The wire 690 can extend through a catheter (e.g., 150 of FIG. 3). The wire 690 can include a tapered distal tip configured to pierce ventricular septum. The lead 600 includes a distal end having a tapered tip, an electrode 660 (e.g., a ring electrode) proximal to the tapered tip, and a helix electrode 620 proximal to the electrode 660. The helix electrode 620 extends from a lead body of the lead 600 and is wrapped around a rod that is connected to the electrode 660. In an embodiment, the rod can include an insulation layer that is non-conductive.

In an embodiment, an outer diameter of the wire 690 can be smaller than an outer diameter of the distal end of the lead 600. In another embodiment, an outer diameter of the wire 690 can be larger than an outer diameter of the distal end of the lead (see FIGS. 16B and 16C). In an embodiment, the wire 690 can include a distal end having an electrode (configured for pacing and/or sensing). It will be appreciated that the wire 690 can help to guide the lead 600 into the heart tissue for deep seating, and/or can provide rail for the lead to slide over the wire 690 to dilate the heart tissue.

Figure 16A:
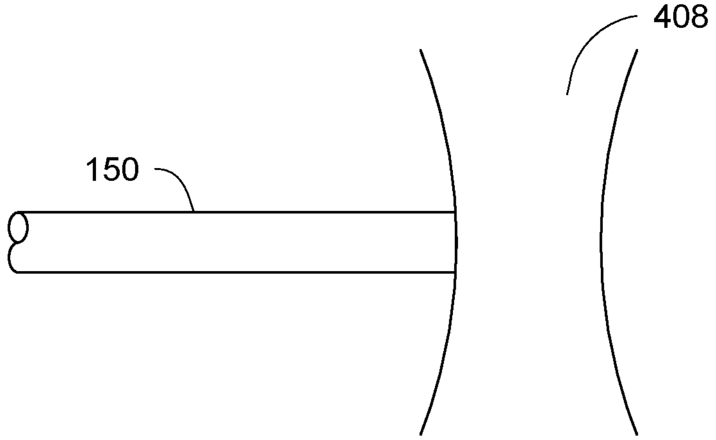
FIGS. 16A-16C illustrate a lead implant procedure, according to an embodiment.
Figure 16B:
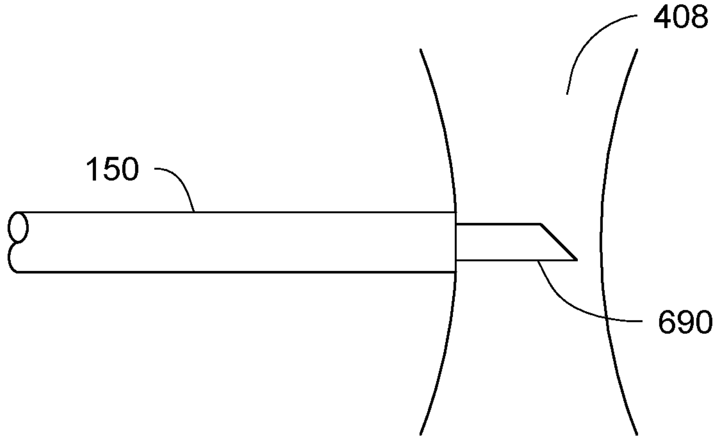
Figure 16C:
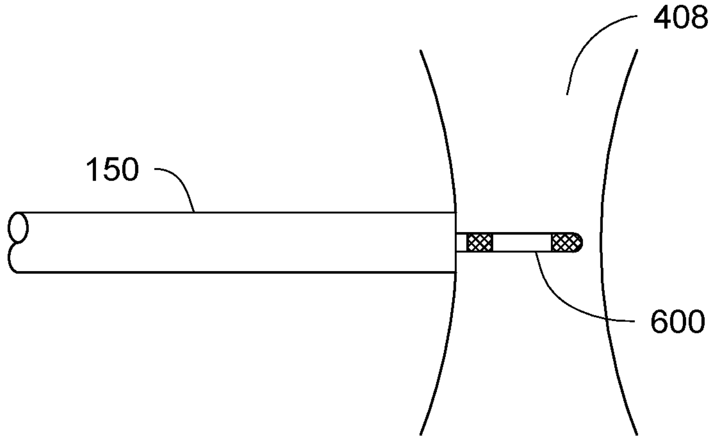

FIGS. 16A-16C illustrate a lead implant procedure, according to an embodiment. A method of implanting a lead for cardiac conduction system using a catheter system can include one or more of the following steps. The method steps for FIG. 16A can be the same as or similar to those as illustrated in FIG. 8A or FIG. 8D. The method includes inserting a catheter 150 to reach the ventricular septum 408, and positioning the catheter 150 against the ventricular septum 408. The method also includes inserting the lead 600 through an orifice of the catheter 150 extending from a distal end of the catheter 150 to a proximal end of the catheter 150, and engaging an electrode of the lead 600 to the ventricular septum 408. The method further includes removing the catheter 150.

As illustrated in FIG. 16B (pre-lead delivery), the method includes before engaging the electrode of the lead 600 to the ventricular septum 408, deploying a needle (a hollow tube with a sharp tip) or wire 690 through the catheter 150 to piece the ventricular septum 408 at a location. The method further includes engaging the electrode of the lead 600 to the location of the ventricular septum 408. In an embodiment, deploying the needle 690 through the catheter 150 to piece the ventricular septum 408 at the location includes conducting pacing through the needle 690 to the ventricular septum 408, conducting sensing to obtain electrocardiogram during or after the pacing, and adjusting the needle 690 to determine the desired location based on the obtained electrocardiogram. The needle 690 can be hold in place (e.g., by an operator such as a physician) when the desired location is identified.

The method includes delivering the lead in the ventricular septum 408 by pushing e.g., the needle or wire 690 through the end of the catheter 150, and pushing the lead through the needle 690. The configuration or structure and/or the method may simplify the implant process (e.g., to facilitate inserting the lead in the ventricular septum 408) and provide more options on how to configure the lead electrodes. Testing shows that penetrating the first at or about 1 millimeter to 2 millimeters of the right ventricular septum inner surface can be difficult due to a thin layer of connective tissue, especially with helix electrodes on distal end of a lead. Piercing the connective tissue with a needle may reduce that challenge.

As illustrated in FIG. 16C, the method includes removing the needle or wire 690 after inserting the lead into the desired location.

Figure 17A:
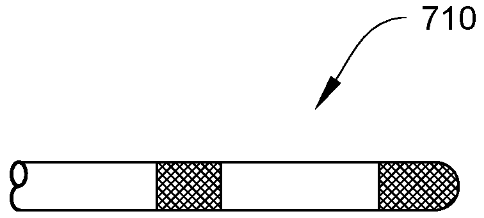
FIGS. 17A-17C illustrate configurations of a distal end of a lead, according to some embodiments.
Figure 17B:
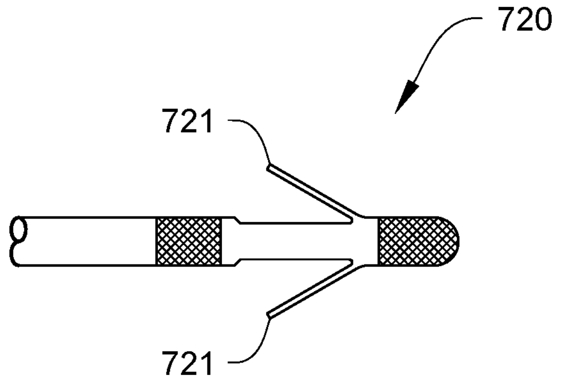
Figure 17C:
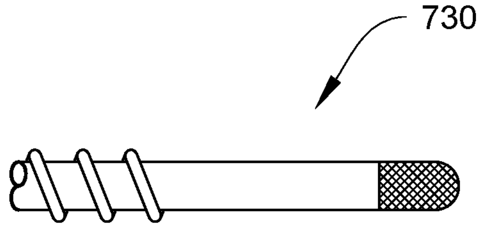

FIGS. 17A-17C illustrate configurations of a distal end (710, 720, and 730) of a lead, according to some embodiments. As shown in FIG. 17A, the lead includes a linear distal end 710 having a distal tip electrode, a second electrode (e.g., a ring electrode), and a non-conductive spacer disposed between the tip electrode and the second electrode. In an embodiment, an outer diameter of the linear distal end 710 ranges from at or about three French to at or about five French. As shown in FIG. 17B, the lead includes a distal end 720 having a distal tip electrode, a second electrode (e.g., a ring electrode), and a non-conductive spacer disposed between the tip electrode and the second electrode. The spacer includes fixation wings 721. As shown in FIG. 17C, the lead includes a linear distal end 730 having a tip electrode, a helix electrode, and a non-conductive spacer disposed between the tip electrode and the helix electrode. The helix electrode wrapped around a portion of the spacer. Embodiments disclosed herein can facilitate deep seating of the lead. For example, the uniformed diameter dual-electrode tip of FIG. 17A can be easily pushed into the heart tissue; wings 721 of FIG. 17B can hold the lead in position so that the lead may be less likely to back out; and the lead configuration of FIG. 17C can provide passive fixation.

Figure 18:
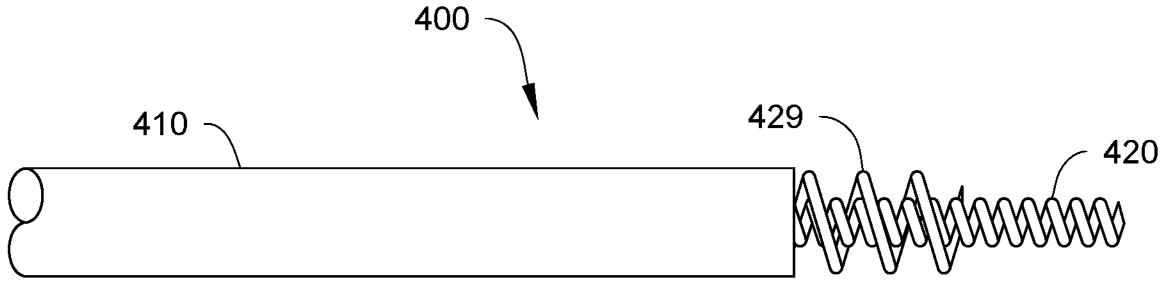
FIG. 18 is a perspective view of a lead, according to an embodiment.

FIG. 18 is a perspective view of a lead 400, according to an embodiment. It will be appreciated that the lead of FIG. 18 can be the same as or similar to the lead of FIG. 10, unless explicitly specified otherwise. As shown in FIG. 18, the distal end of the lead 400 only includes two helix electrodes (420, 429). That is, there is no spacer or the linear electrode. An outer diameter of the helix electrode 420 can be smaller than an outer diameter of the helix electrode 429. Spacing between windings of the coil of the helix electrode 429 can be greater than spacing between windings of the coil of the helix electrode 420. In another embodiment, spacing between windings of the coil of the helix electrode 429 can be the same as or smaller than spacing between windings of the coil of the helix electrode 420.

In an embodiment, the lead 400 can include a ring electrode (e.g., 230 of FIG. 4C, 330 of FIGS. 5 and 11, or the like) and a spacer (e.g., 240 of FIG. 4C, 340 of FIG. 5, or the like). In an embodiment, the length of the helix electrode 429 (extending from the lead body 410) can be the same as or similar to the length of the core 225 of FIG. 4C. The length of the helix electrode 420 (extending from the lead body 410) can be the same as or similar to the length of the helix electrode 220 of FIG. 4C. In an embodiment, the length of the helix electrode 429 can be the same as, short than, or slightly longer than the length of the helix electrode 420.

In an embodiment, a portion (e.g., proximal or distal portion) of the helix electrode 420 and/or the helix electrode 429 can be non-conductive (e.g., coated with electrical insulating material or the like). In an embodiment, the portion of the helix electrode 420 and/or the helix electrode 429 that is conductive or active (which can be served as electrode) can have a length of at or about two millimeters. In an embodiment, a distance between the distal tip of helix electrode 420 and the distal tip of helix electrode 429 can range from at or about two millimeters to at or about six millimeters.

In an embodiment, the length of the helix electrode 429 can range from e.g., at or about two millimeters to at or about six millimeters. The length of the helix electrode 420 can range from e.g., at or about four millimeters to at or about 12 millimeters.

In an embodiment, the helix electrode 420 and/or the helix electrode 429 can have a fixed length. In another embodiment, the helix electrode 420 and/or the helix electrode 429 can be extendable and/or retractable.

It will be appreciated that the helix electrode 420 and the helix electrode 429 can be controlled or operated (e.g., by rotating a corresponding pin or any suitable control mechanism at the proximal end of the lead) independent to each other to advance into the septum, extend distally, and/or retract proximally. In another embodiment, the helix electrode 420 and the helix electrode 429 can be controlled or operated together by a pin or any suitable control mechanism to advance into the septum, extend distally, and/or retract proximally.

It will be appreciated that a fixed length of an electrode may refer to the length of the electrode extending distally from the distal end of the lead body being constant. An electrode being extendable may refer to the electrode being distally extendable from the distal end of the lead body so that the length of the electrode extending distally from the distal end of the lead body can be increased (e.g., to its maximum allowable length). An electrode being retractable may refer to the electrode being proximally retractable from the distal end of the lead body so that the length of the electrode extending distally from the distal end of the lead body can be decreased (e.g., to its minimum value of zero).

In an embodiment, the lead can be delivered using e.g., at or about or larger than 6 French inner diameter sheath or catheter, a guide wire, or a stylet. In an embodiment, the ring electrode described herein can have a cylinder shape or be a closed coil or any other suitable shape.

It will also be appreciated that with dual-helix electrodes design (e.g., FIG. 10 and FIG. 18), the two helix electrode can be co-radial, co-axial, or both. For example, in FIG. 18, the two helix electrodes (420, 429) share a same axis in a length direction of the lead, and the two helix electrodes (420, 429) are co-axial. In FIG. 10, the two helix electrodes (420, 429) share a same diameter or radii in a radial direction of the lead, and the two helix electrodes (420, 429) are co-radial. It will be appreciated that the two helix electrodes (420, 429) of FIG. 10 are also co-axial. Co-radial helix electrodes can be made of small size to facilitate the implant process. Co-axial helix electrodes can facilitate advancing each helix electrode separately (i.e., maneuver of advancing each helix electrode is independent to each other).

It will further be appreciated that the different number of electrodes can provide bipolar, tri-polar, and/or quad-polar sensing and pacing capabilities.

Embodiments disclosed herein can help to easily place the lead deep into the interventricular septum (i.e., the ventricular septum) to target/locate the conduction pathway(s) such as LBB, can reduce (or produce less) heart tissue trauma and may result in a lower and stable pacing threshold, and/or can provide secured lead fixation with chronic lead stability.

ASPECTS

It is appreciated that any one of aspects can be combined with other aspect(s).

Aspect 1. A catheter system for implanting a lead for cardiac conduction system, the catheter system comprising:

a catheter having an orifice extending from a distal end of the catheter to a proximal end of the catheter for implanting the lead; and a probe extending through the catheter, wherein the probe includes a conductive wire covered with an insulation layer, a distal end of the wire is exposed from the insulation layer, the distal end of the wire includes an electrode configured to conduct pacing prior to implanting the lead.

Aspect 2. The catheter system according to aspect 1, wherein the catheter further includes a first opening separated from the orifice, the first opening extends from the distal end of the catheter to the proximal end of the catheter for inserting the probe, and the electrode is cathode.

Aspect 3. The catheter system according to aspect 2, wherein the distal end of the catheter has a fixed curve.

Aspect 4. The catheter system according to aspect 2, wherein the catheter further includes a second opening and a third opening, the second opening is configured to accommodate a first deflection wire, the third opening is configured to accommodate a second deflection wire, the first deflection wire and the second deflection wire are configured to be pulled to deflect the distal end of the catheter.

Aspect 5. The catheter system according to aspect 4, wherein the first deflection wire is configured to be pulled to deflect the distal end of the catheter in a first plane, the second deflection wire is configured to be pulled to deflect the distal end of the catheter in a second plane perpendicular to the first plane.

Aspect 6. The catheter system according to aspect 4, wherein the first deflection wire is configured to be pulled to deflect a tip of the distal end of the catheter, the second deflection wire is configured to be pulled to deflect a location of the distal end of the catheter, the location being separate from and proximal to the tip of the distal end of the catheter.

Aspect 7. The catheter system according to aspect 4, wherein the first deflection wire and the second deflection wire are spaced apart at or about 90 degrees central angle from a center of the catheter in a cross-sectional view.

Aspect 8. The catheter system according to any one of aspects 1-7, wherein the probe is mounted to the catheter, and the electrode is cathode.

Aspect 9. The catheter system according to any one of aspects 1-8, wherein the wire is further configured to conduct sensing prior to implanting the lead.

Aspect 10. The catheter system according to any one of aspects 1-9, wherein the wire has a diameter ranging from at or about 100 micron to at or about 150 micron.

Aspect 11. The catheter system according to any one of aspects 1-10, wherein the wire is radiopaque.

Aspect 12. The catheter system according to any one of aspects 1-11, wherein a proximal end of the wire is exposed from the insulation layer.

Aspect 13. The catheter system according to any one of aspects 1-12, wherein at or about one millimeter to at or about three millimeters of the distal end of the wire is exposed from the insulation layer.

Aspect 14. The catheter system according to any one of aspects 1-13, wherein the insulation layer has a thickness of at or about 25 micron.

Aspect 15. The catheter system according to any one of aspects 1-14, wherein the insulation layer is made of polytetrafluoroethylene or polyimide.

Aspect 16. A method of implanting a lead for cardiac conduction system using a catheter system, the method comprising:

inserting a catheter to reach septum;

placing a probe to reach and electrically map the cardiac conduction system, the probe including a conductive wire covered with an insulation layer, a distal end of the wire being exposed from the insulation layer, the distal end of the wire including an electrode;

dispositioning the probe into the septum;

conducting pacing through the probe to the septum;

conducting sensing to obtain electrocardiogram during or after the pacing;

adjusting a location of the probe based on the obtained electrocardiogram;

inserting the lead through an orifice of the catheter extending from a distal end of the catheter to a proximal end of the catheter; and placing a distal end of the lead to the adjusted location.

Aspect 17. The method according to aspect 16, further comprising:

pulling a first deflection wire to deflect the distal end of the catheter;

pulling a second deflection wire to further deflect the distal end of the catheter;

positioning a tip of the distal end of the catheter to be perpendicular to an endocardial surface of the septum.

Aspect 18. The method according to aspect 17, wherein pulling the first deflection wire to deflect the distal end of the catheter includes pulling the first deflection wire to deflect the distal end of the catheter in a first plane;

pulling the second deflection wire to further deflect the distal end of the catheter includes pulling the second deflection wire to deflect the distal end of the catheter in a second plane perpendicular to the first plane.

Aspect 19. The method according to aspect 17, wherein pulling the first deflection wire to deflect the distal end of the catheter includes pulling the first deflection wire to deflect a tip of the distal end of the catheter;

pulling the second deflection wire to further deflect the distal end of the catheter includes pulling the second deflection wire to deflect a location of the distal end of the catheter, the location being separate from and proximal to the tip of the distal end of the catheter.

Aspect 20. The method according to any one of aspects 16-19, wherein placing the probe to reach the septum including inserting the probe through an opening of the catheter extending from the distal end of the catheter to the proximal end of the catheter.

Aspect 21. The method according to any one of aspects 16-20, wherein placing the probe to reach the septum including attaching the probe to the catheter.

Aspect 22. A lead for cardiac conduction system, the lead comprising:

a lead body having a first diameter;

a distal end including a helix electrode having a second diameter; and a proximal end, wherein the second diameter is equal to, smaller than, or greater than the first diameter.

Aspect 23. The lead according to aspect 22, wherein a length of the helix electrode is at or about four millimeters.

Aspect 24. The lead according to aspect 22 or aspect 23, wherein the helix electrode includes a solid core having a tapered tip.

Aspect 25. The lead according to any one of aspects 22-24, wherein the helix electrode is a bipolar electrode.

Aspect 26. The lead according to any one of aspects 22-25, further comprising a ring electrode proximal to the helix electrode.

Aspect 27. A lead for cardiac conduction system, the lead comprising:

a lead body;

a distal end including a linear electrode having a tapered tip and a rod integral to the tapered tip; and a proximal end, wherein a helix wire is wrapped around the rod of the linear electrode.

Aspect 28. The lead according to aspect 27, further comprising a ring electrode proximal to the linear electrode.

Aspect 29. A lead for cardiac conduction system, the lead comprising:

a lead body;

a distal end including a linear electrode having a tapered tip and a rod integral to the tapered tip, a spacer connected to the linear electrode, and a helix electrode fixed to the lead body; and a proximal end, wherein the spacer is adjustable to distally extend or proximally retract the linear electrode.

Aspect 30. The lead according to aspect 29, wherein the helix electrode is a bipolar electrode including a distal cathode, a non-conductive middle portion, and a proximal anode.

Aspect 31. The lead according to aspect 30, wherein the helix electrode has a length of at or about four millimeters, the distal cathode has a length of at or about one millimeter, the non-conductive middle portion has a length of at or about two millimeters, and the proximal anode has a length of at or about one millimeter.

Aspect 32. The lead according to any one of aspects 29-31, wherein the linear electrode is a bipolar electrode including a distal cathode, a non-conductive middle portion, and a proximal anode.

Aspect 33. The lead according to aspect 32, wherein the linear electrode has a length of at or about four millimeters, the distal cathode has a length of at or about one millimeter, the non-conductive middle portion has a length of at or about two millimeters, and the proximal anode has a length of at or about one millimeter.

Aspect 34. The lead according to any one of aspects 29-33, wherein an outer surface of the linear electrode is threaded.

Aspect 35. The lead according to any one of aspects 29-34, wherein the linear electrode is cathode, and the helix electrode is anode.

Aspect 36. The lead according to aspect 35, wherein the linear electrode includes a proximal coated region and an uncoated tip.

Aspect 37. The lead according to any one of aspects 29-36, wherein an outer diameter of the linear electrode ranges from at or about three French to at or about five French.

Aspect 38. The lead according to any one of aspects 29-37, wherein the spacer is flexible.

Aspect 39. The lead according to any one of aspects 29-38, further comprising a second helix electrode fixed to the lead body, a coil of the helix electrode and a coil of the second helix electrode extend distally from the lead body and wind alongside with each other, the coil of the helix electrode extends further distally than the coil of the second helix electrode.

Aspect 40. The lead according to aspect 39, wherein the helix electrode is cathode and the second helix electrode is anode.

Aspect 41. The lead according to any one of aspects 29-40, further comprising a ring electrode proximal to the helix electrode.

Aspect 42. The lead according to any one of aspects 29-41, wherein the helix electrode is a bipolar electrode including a distal portion and a proximal portion, the distal portion is non-conductive and the proximal portion is conductive.

Aspect 43. The lead according to aspect 42, wherein the helix electrode has a length of at or about four millimeters, the distal portion has a length of at or about two millimeters, and the proximal portion has a length of at or about two millimeters.

Aspect 44. The lead according to any one of aspects 29-43, wherein the spacer includes an insulation layer, a second helix electrode extends from the lead body and is winded over the insulation layer, the second helix electrode has an outer diameter smaller than an outer diameter of the helix electrode.

Aspect 45. The lead according to aspect 44, wherein the linear electrode is cathode, the second helix electrode is anode, and the helix electrode is cathode.

Aspect 46. A method of implanting a lead for cardiac conduction system using a catheter system, the method comprising:

inserting a catheter to reach ventricular septum;

positioning the catheter against the ventricular septum;

inserting the lead through an orifice of the catheter extending from a distal end of the catheter to a proximal end of the catheter;

rotating a lead body of the lead to engage a helix electrode of the lead to the ventricular septum; and removing the catheter.

Aspect 47. The method according to aspect 46, further comprising:

partially engaging a linear electrode of the lead to the ventricular septum; and rotating a pin to extend and deploy the linear electrode of the lead into the ventricular septum.

Aspect 48. A lead for cardiac conduction system, the lead comprising:

a lead body;

a distal end including and a first helix electrode and a second helix electrode; and a proximal end, wherein the first helix electrode and the second helix electrode are fixed to the lead body, a coil of the first helix electrode and a coil of the second helix electrode extend distally from the lead body and wind alongside with each other, the coil of the first helix electrode extends further distally than the coil of the second helix electrode.

Aspect 49. The lead according to aspect 48, wherein a portion of the first helix electrode is insulated and is not electrically conductive.

Aspect 50. The lead according to aspect 48 or aspect 49, wherein the first helix electrode is configured for drug elution.

Aspect 51. The lead according to any one of aspects 48-50, wherein the first helix electrode is configured as a pacing electrode and/or a sensing electrode.

Aspect 52. The lead according to any one of aspects 48-51, wherein a portion of the second helix electrode is insulated and is not electrically conductive.

Aspect 53. The lead according to any one of aspects 48-52, wherein the second helix electrode is configured for drug elution.

Aspect 54. The lead according to any one of aspects 48-53, wherein the second helix electrode is configured as a pacing electrode and/or a sensing electrode.

Aspect 55. The lead according to any one of aspects 48-54, wherein the lead further includes a drug collar at a lead body tip proximal to the first helix electrode and the second helix electrode.

Aspect 56. A lead for cardiac conduction system, the lead comprising:

a lead body;

a distal end including a linear electrode having a tapered tip and a rod integral to the tapered tip, a helix electrode fixed to the lead body, and a spacer disposed between the linear electrode and the helix electrode; and a proximal end, wherein a length of the spacer is predetermined.

Aspect 57. The lead according to aspect 56, further comprising a ring electrode proximal to the helix electrode.

Aspect 58. A lead assembly for cardiac conduction system, the lead assembly comprising:

a lead having a lead body, a distal end, and a proximal end; and a connector separate from the lead, wherein an outer diameter of the lead body is equal to or greater than an outer diameter of the proximal end, the outer diameter of the lead body is equal to or greater than an outer diameter of the distal end;

the proximal end is configured to connect to a first end of the connector, a second end of the connector is configured to connect to a header of an implantable pulse generator.

Aspect 59. The lead assembly according to aspect 58, wherein the second end of the connector is an IS-1, IS-4, or DF-4 connector.

Aspect 60. A catheter system for implanting a lead for cardiac conduction system, the catheter system comprising:

a catheter having an orifice extending from a distal end of the catheter to a proximal end of the catheter for implanting the lead; and a wire extending through the catheter, wherein the wire includes a tapered distal tip configured to pierce septum.

Aspect 61. The catheter system according to aspect 60, wherein the lead includes a distal end having a tapered tip, a ring electrode proximal to the tapered tip, and a helix electrode proximal to the ring electrode, the helix electrode extends from a lead body of the lead and is wrapped around a rod that is connected to the ring electrode.

Aspect 62. The catheter system according to aspect 61, wherein an outer diameter of the wire is smaller than an outer diameter of the distal end of the lead.

Aspect 63. The catheter system according to aspect 61, wherein an outer diameter of the wire is larger than an outer diameter of the distal end of the lead.

Aspect 64. The catheter system according to any one of aspects 60-63, wherein the lead includes a linear distal end having a tip electrode, a second electrode, and a non-conductive spacer disposed between the tip electrode and the second electrode, an outer diameter of the linear distal end ranges from at or about three French to at or about five French.

Aspect 65. The catheter system according to any one of aspects 60-64, wherein the lead includes a distal end having a tip electrode, a second electrode, and a non-conductive spacer disposed between the tip electrode and the second electrode, the spacer includes fixation wings.

Aspect 66. The catheter system according to any one of aspects 60-65, wherein the lead includes a linear distal end having a tip electrode, a helix electrode, and a non-conductive spacer disposed between the tip electrode and the helix electrode.

Aspect 67. The catheter system according to any one of aspects 60-66, wherein the wire includes a distal end having an electrode.

Aspect 68. A method of implanting a lead for cardiac conduction system using a catheter system, the method comprising:

inserting a catheter to reach septum;

positioning the catheter against the septum;

inserting the lead through an orifice of the catheter extending from a distal end of the catheter to a proximal end of the catheter;

engaging an electrode of the lead to the septum;

removing the catheter.

Aspect 69. The method according to aspect 68, further comprising:

before engaging the electrode of the lead to the septum, deploying a wire through the catheter to piece the septum at a location;

engaging the electrode of the lead to the location of the septum; and removing the wire.

Aspect 70. The method according to aspect 69, wherein deploying the wire through the catheter to piece the septum at the location includes:

conducting pacing through the wire to the septum;

conducting sensing to obtain electrocardiogram during or after the pacing;

adjusting the wire to determine the location based on the obtained electrocardiogram.

The terminology used in this specification is intended to describe particular embodiments and is not intended to be limiting. The terms "a," "an," and "the" include the plural forms as well, unless clearly indicated otherwise. The terms "comprises" and/or "comprising," when used in this specification, specify the presence of the stated features, integers, steps, operations, elements, and/or components, but do not preclude the presence or addition of one or more other features, integers, steps, operations, elements, and/or components.

With regard to the preceding description, it is to be understood that changes may be made in detail, especially in matters of the construction materials employed and the shape, size, and arrangement of parts without departing from the scope of the present disclosure. This specification and the embodiments described are exemplary only, with the true scope and spirit of the disclosure being indicated by the claims that follow.

What is claimed is:

1. A lead for cardiac conduction system, the lead comprising:

a proximal end;

a lead body extending from the proximal end; and a distal end extending from the lead body, wherein the lead body includes a non-conductive spacer, the distal end includes a helix electrode distal to the spacer, the lead further includes a ring electrode proximal to the spacer and surrounding a portion of the lead body, the helix electrode includes a core disposed within a helical space of the helix electrode, the core has a cone-shape tip and a rod integral to the tip, and the core is non-conductive.

2. The lead according to claim 1, wherein the core includes a hollow body configured to accommodate drug for elution, the core has a porous surface configured for drug elution.

3. The lead according to claim 1, wherein the lead body has an outer diameter of less than or equal to five French.

4. The lead according to claim 1, wherein a length of the helix electrode distal to the lead body ranges from at or about 2.2 millimeters to at or about 2.6 millimeters.

5. The lead according to claim 1, wherein the helix electrode is a bipolar electrode including a distal electrode, a non-conductive middle portion, and a proximal electrode.

6. The lead according to claim 1, wherein the helix electrode includes a distal portion and a proximal portion, the distal portion is conductive and uncoated, and the proximal portion is non-conductive and coated with an electrical insulating material.

7. The lead according to claim 1, wherein the spacer is adjustable to distally extend or proximally retract the helix electrode.

* * * * *